US006593304B1

(12) United States Patent
Hasegawa et al.

(10) Patent No.: US 6,593,304 B1
(45) Date of Patent: *Jul. 15, 2003

(54) RECOMBINANT DNA COMPRISING DNA CODING FOR MYOSIN HEAVY CHAIN SM1 ISO-FORM PROTEIN INSERTED INTO VECTOR DNA MICROORGANISM CARRYING THE RECOMBINANT DNA, AND AN AGENT FOR TREATMENT OF ARTERIOSCLEROSIS COMPRISING THE RECOMBINANT DNA

(75) Inventors: Kazuhide Hasegawa, Tokyo (JP); Emi Arakawa, Tokyo (JP); Shoji Oda, Kanagawa (JP); Yuzuru Matsuda, Tokyo (JP); Katsuhito Takahashi, Osaka (JP); Michihiro Sugahara, Shizuoka (JP); Haruo Ishiyama, Kanagawa (JP)

(73) Assignees: Vessell Research Laboratory Co. Ltd., Tokyo (JP); Osaka Prefectual Government, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,435

(22) PCT Filed: Jan. 25, 1996

(86) PCT No.: PCT/JP96/00134

§ 371 (c)(1),
(2), (4) Date: Jul. 25, 1997

(87) PCT Pub. No.: WO96/23069

PCT Pub. Date: Aug. 1, 1996

(30) Foreign Application Priority Data

Jan. 25, 1995 (JP) .............................................. 7-010085

(51) Int. Cl.[7] ........................ C07H 21/00; A61K 48/00; C12N 15/12; C12N 15/65
(52) U.S. Cl. ........................ 514/44; 424/93.2; 435/455; 435/320.1
(58) Field of Search ........................ 514/44; 424/93.2; 435/320.1, 172.3, 455, 325, 252.3; 536/23.1, 23.5

(56) References Cited

FOREIGN PATENT DOCUMENTS

JP              06046841 A     2/1994

OTHER PUBLICATIONS

Ngo et al., "Computational complexity, protein structure prediction, and the Levinthal paradox", in 'The Protein Folding Problem and Tertiary Structure Prediction', Merz et al. (eds.), Birkhauser Boston: Boston, MA, pp. 433 & 492–495, 1994.*

Smith, "Viral vectors in gene therapy", Annu. Rev. Microbiol. 49, pp. 807, 815–816, 1995.*

Lafont et al., "Which gene for which restenosis", Lancet 346: 1442–1443, Dec. 1995.*

Kaufman, "Vectors used for expression in mammalian cells", Meth. Enzymol. 185: 487–511, 1990.*

Kelley et al., "Characterization of isoform diversity in smooth muscle myosin heavy chains", Can. J. Physiol. Pharmacol. 72(11): 1351–1360, Nov. 1994.*

Niwa et al., "Efficient selection for high–expression transfectants with a novel eukaryotic vector", Gene 108(2): 193–199, Dec. 1991.*

Kuro–O M. et al., "Developmentally regulated expression of vascular smooth muscle myosin heavy chain isoforms" J. Biol. Chem. vol. 264, No. 31, Nov. 5, 1989, pp. 18272–18275.

Szent–Gyorgyi et al., "Light Meromyosin Fraction I: A helical Molecule from Myosin", *J. Mol. Biol.* 2:133–142 (1960).

Lowey et al., "Substructure of the Myosin Molecule", *J. Mol. Biol.* 42:1–29 (1969).

Nagai et al., "Identification of Two Types of Smooth Muscle Myosin Heavy Chain Isoforms by cDNA Cloning and Immunoblot Analysis", *J. Biol. Chem.* vol. 264, No. 17, pp. 9734–9737, 1989.

Babij et al., Characterization of a mammalian smooth muscle myosin heavy–chain gene, *Proc. Natl. Acad. Sci.*, USA vol. 88, pp. 10676–10, 680 , 1991.

* cited by examiner

*Primary Examiner*—Scott D. Priebe
(74) *Attorney, Agent, or Firm*—Fish & Richardson P.C.

(57) ABSTRACT

The present invention relates to recombinant DNA comprising DNA coding for smooth-muscle-type myosin heavy chain SM1 isoform protein inserted into vector DNA, a microorganism carrying the recombinant DNA, and an agent for treatment of arteriosclerosis comprising the recombinant DNA. The recombinant DNA of the present invention can be used effectively as an agent for gene therapy of restenosis after PTCA treatment.

16 Claims, 4 Drawing Sheets

CODE

RECOMBINANT DNA COMPRISING DNA CODING FOR MYOSIN HEAVY CHAIN SM1 ISO-FORM PROTEIN INSERTED INTO VECTOR DNA MICROORGANISM CARRYING THE RECOMBINANT DNA, AND AN AGENT FOR TREATMENT OF ARTERIOSCLEROSIS COMPRISING THE RECOMBINANT DNA

TECHNICAL FIELD

The present invention relates to recombinant DNA comprising DNA coding for myosin heavy chain SM1 isoform protein inserted into vector DNA, a microorganism carrying the recombinant DNA and an agent for treatment of arteriosclerosis comprising the recombinant DNA which are used in gene therapy.

BACKGROUND ART

Smooth muscle-type myosin heavy chain SM1 isoform protein is responsible for contraction and relaxation of smooth muscles, and is one of the myosin heavy chain isoform proteins expressed specifically in smooth muscle cells. As the DNA coding for the protein, the nucleotide sequence of cDNA coding for rabbit SM1 isoform is known (P. Babij et al.: Proc. Natl. Acad. Sci. USA, 88, 10676 (1991)), but there is not known any homology among nucleotide sequences for such DNAs. Further, there is not known any recombinant DNA comprising DNA coding for smooth muscle-type myosin heavy chain SM1 isoform protein inserted into vector DNA which recombinant DNA can be injected into animal cells.

It has been reported that when cDNA coding for a protein called calponin which is a protein existing in smooth muscle cells is introduced and expressed in a vascular smooth muscle cell line derived from rat pulmonary arteries, the time required for doubling the cells is prolonged by about 4 hours (Takahashi et al.: Circulation, 88, I-174 (1993)) and that when cDNA for human calponin is injected into a rabbit topically at a site where the carotid artery has been abraded with a balloon, thickening of the intima is inhibited (Takahashi et al.: Circulation, 88, I-656 (1993)). It is not known that recombinant DNA comprising DNA coding for myosin heavy chain SM1 isoform protein inserted into vector DNA has pharmacological effect and is used for in gene therapy.

For treatment of arteriosclerosis, percutaneous transluminal coronary angioplasty (PTCA) in which a stenosed site is enlarged by a balloon catheter is extensively conducted. The treatment method has the advantages of easier operation and higher degree of success than the bypass surgery etc., while the treatment method has the disadvantage that 30 to 40% of the patients after the treatment suffer from restenosis of blood vessels due to abnormal proliferation of vascular cells. Therefore, there is demand for developments in an agent for treatment of arteriosclerosis effectively used for preventing such restenosis.

DISCLOSURE OF THE INVENTION

The present invention includes:
(1) A recombinant DNA comprising DNA coding for smooth muscle-type myosin heavy chain SM1 isoform protein inserted into vector DNA.
(2) The recombinant DNA according to (1) wherein the vector DNA is a retrovirus vector, adenovirus vector, adeno-associated virus vector or a plasmid capable of being expressed in an animal.
(3) The recombinant DNA according to (2) wherein the plasmid capable of being expressed in an animal is pCXN2 or PAGE208.
(4) The recombinant DNA according to any one of (1) to (3) wherein the smooth muscle-type myosin heavy chain SM1 isoform protein is of a human smooth muscle type, rabbit muscle type or mouse muscle type.
(5) The recombinant DNA according to any one of (1) to (3) wherein the DNA coding for smooth muscle-type myosin heavy chain SM1 isoform protein is the nucleotide sequence shown in SEQ ID NO:1, or the nucleotide sequence shown in SEQ ID NO:1 in which at least one nucleotide is added, deleted or replaced.
(6) DNA coding for smooth muscle-type myosin heavy chain SM1 isoform protein, which is the nucleotide sequence shown in SEQ ID NO:1, or the nucleotide sequence shown in SEQ ID NO:1 in which at least one nucleotide is added, deleted or replaced.
(7) A microorganism carrying the recombinant DNA of (5).
(8) The microorganism according to (7) which belongs to the genus Escherichia.
(9) An agent for treatment of arteriosclerosis which comprises the recombinant DNA of any one of (1) to (5).

The DNA coding for smooth muscle-type myosin heavy chain SM1 isoform protein includes cDNA or genomic DNA coding for smooth muscle-type myosin heavy chain SM1 isoform protein, preferably DNA derived from humans, rabbits, mice, etc.

The nucleotide sequence of the DNA coding for smooth muscle-type myosin heavy chain SM1 isoform protein includes the nucleotide sequence of cDNA (SEQ ID NO:5) coding for rabbit SM1 isoform protein (SEQ ID NO:4) (Proc. Natl. Acad. Sci. USA, 88, 10676 (1991)), the nucleotide sequence of the DNA coding for mouse myosin heavy chain SM1 isoform protein as shown in SEQ ID NO:1, and the nucleotide sequence as shown in SEQ ID NO:2 which is specified by homologous regions between the above nucleotide sequences (In the Sequence Listing, Y represents T, U or C; S represents G or C; V represents A, G or C; B represents B, C, T or U; W represents A, T, or U; N represents A, C, G, T, U or a single bond; and the codon YAS (388–390) represents TAC or CAG.). Accordingly, the nucleotide sequence shown in SEQ ID NO:2 contains the nucleotide sequence of SEQ ID NO:1 and the nucleotide sequence of the cDNA coding for rabbit SM1 isoform protein. A partial nucleotide sequence of cDNA coding for human smooth muscle-type myosin heavy chain SM1 isoform protein is also known (Amer. J. of Medical Genetics, 46, 61–67 (1993)), and a nucleotide sequence of this partial nucleotide sequence combined with a partial nucleotide sequence of SEQ ID NO:2 is also contained in the nucleotide sequence of the DNA coding for smooth muscle-type myosin heavy chain SM1 isoform protein according to the present invention.

Further, the nucleotide sequence of SEQ ID NO:2 or the combination of a partial nucleotide sequence of SEQ ID NO:2 and the nucleotide sequence of the DNA derived from human smooth muscles, in which one or more nucleotides have been added, deleted or replaced by means of site-directed mutagenesis (Nucleic Acid Research, 10, 6487–6508 (1982)), is also contained in the nucleotide sequence of the DNA coding for smooth muscle-type myosin heavy chain SM1 isoform protein according to the present invention.

The vector DNA that can be used includes virus vectors such as retrovirus vector, adenovirus vector and adeno-associated virus vector and plasmids capable of being expressed in an animal such as pCXN2 (Gene, 108, 193–200 (1991)) and PAGE207 (Japanese Patent Laid-Open Publication No. 46841/1994) as well as their modified vectors.

The agent for treatment of arteriosclerosis according to the present invention can be produced by compounding the recombinant DNA comprising DNA coding for smooth muscle-type myosin heavy chain SM1 isoform protein inserted into vector DNA as an active ingredient together with a base used in agents for gene therapy. Just before administration, the pharmaceutical preparation can be used in gene therapy for arteriosclerosis, if necessary after encapsulation in liposomes etc. (Proc. Natl. Acad. Sci. USA., 90, 11307 (1993)).

Where the DNA coding for smooth muscle-type myosin heavy chain SM1 isoform protein is inserted into a virus vector, a therapeutic agent can be produced by preparing virus particles containing the recombinant DNA and then compounding them together with a base used in agents for gene therapy (Nature Genet., 8, 42(1994)).

The base used in agents for gene therapy may be any base generally used in injections. The base includes, for example, distilled water, a salt solution of sodium chloride, a mixture of sodium chloride and an inorganic salt, or the like, solutions of mannitol, lactose, dextran, glucose, etc., solutions of amino acid such as glycine, arginine, etc., a mixed solution of an organic acid solution or a salt solution and glucose solution, and the like. Further, injections may be prepared in a usual manner as a solution, suspension or dispersion by adding adjuvant such as an osmotic pressure controlling agent, pH adjusting agent, vegetable oils such as sesame oil, soybean oil, etc. or surface active agents such as lecithin, non-ionic surface active agent, etc. to the above base. These injections can also be powdered, lyophilized, etc. to be dissolved just before use.

The agent for treatment of arteriosclerosis can be used as such in the case of a solution, and in the case of a solid it is dissolved in the base previously sterilized if necessary just before use in gene therapy.

The method for administration of the agent for treatment of arteriosclerosis according to the present invention involves topically administrating it into a patients who underwent the PTCA treatment, at a dose of 1 ng to 1 g per day or once after the surgery by means of a catheter etc. such that it can be absorbed into their vascular smooth muscle cells at the target site.

The agent for treatment of arteriosclerosis according to the present invention is safe in this dose range.

Hereinafter, the process for producing the recombinant DNA comprising DNA coding for smooth muscle-type myosin heavy chain SM1 isoform protein inserted into vector DNA is described.

The recombinant DNA comprising DNA coding for smooth muscle-type myosin heavy chain SM1 isoform protein inserted into vector DNA can be obtained according to the usual genetic engineering method described below or its modified method.

A DNA clone coding for smooth muscle-type myosin heavy chain SM1 isoform protein is detected in a cDNA library from tissues composed mainly of smooth muscles in the uterus, aorta, etc., according to the method described by A. Abe et al. (ECL direct DNA labeling detection system manual (Amersham)).

The recombinant DNA comprising the inserted DNA coding for myosin heavy chain SM1 isoform protein can be produced by ligating said DNA fragment to a downstream region from a promoter in a suitable vector DNA (J. Sambrook et al., Molecular Cloning, 2nd Ed., Vol. 1, Cold Spring Harbor Laboratory Press (1989)). Animal cells are used as a host, and a promoter derived from SV40, a promoter from retrovirus, a metallothionein promoter, β-actin promoter etc. can be utilized as the promoter. For the expression, the use of an enhancer is also effective.

The reaction conditions for the above-mentioned recombinant techniques are as follows: The digestion of DNA with a restriction enzyme is carried out by allowing the restriction enzyme in an amount of 0.1 to 100 units, preferably 1 to 3 units per $\mu$g DNA to act on 0.1 to 20 $\mu$g DNA in a reaction solution usually containing 2 to 200 mM preferably 10 to 40 mM Tris-HCl buffer, pH 6.0 to 9.5, preferably pH 7.0 to 8.0, 0 to 200 mM sodium chloride, and 2 to 20 mM preferably 5 to 10 mM magnesium chloride, at 20 to 70° C. (the optimum temperature is varied depending on the restriction enzyme used) for 15 minutes to 24 hours. The termination of the reaction can be effected usually by heating the reaction solution at 55 to 75° C. for 5 to 30 minutes or by inactivating the restriction enzyme with reagents such as phenol etc. The DNA fragment, or the gapped duplex DNA, generated by digestion with the restriction enzyme can be purified using Prep-A-Gene Matrix (Bio-Rad). The ligation of the DNA fragment can be effected using a DNA ligation kit (Takara Shuzo Co., Ltd.).

The recombinant DNA containing DNA coding for smooth muscle-type myosin heavy chain SM1 isoform protein thus constructed in this manner is used to produce a transformant.

The host for the plasmid capable of being expressed in an animal includes, for example, microorganisms belonging to the genus Escherichia, such as *Escherichia coli* K12·HB101 (H. W. Boyer et al.: J. Mol. Biol.,41, 459 (1969)), DH5 α (D. Hanahan: J. Mol. Biol., 166, 557 (1983)) etc. The transformation of microorganisms of the genus Escherichia can be effected according to the method of Cohen et al. (S. N. Cohen et al.: Proc. Natl. Acad. Sci. USA, 69, 2110 (1972)).

The host used for the virus vector includes animal cells having the ability to produce viruses, such as monkey cell COS-7, Chinese hamster cell CHO, mouse cell BALB/3T3, human cell HeLa, etc.; the host for the retrovirus vector includes ΨCRE, ΨCRIP (Proc. Natl. Acad. Sci. USA, 85, 6460 (1988)), MLV (J. Virol., 65, 1202 (1991)) etc.; and the host for the adenovirus vector and adeno-associated virus vector includes 293 cells derived from human fetal kidney ("jikken Igaku" (Experimental Medicine), 12, 316 (1994)) etc. The introduction of the virus vector into animal cells can be effected using the calcium phosphate method (Virology, 52, 456 (1973)) etc.

The resulting transformant can be cultured in the following manner depending on the difference in the cell species to produce the recombinant DNA.

To culture the transformant from a microorganism of the genus Escherichia as the host, the suitable medium is a liquid medium containing a carbon source, nitrogen source, inorganic substance, etc. necessary for the growth of the transformant. The carbon source includes e.g. glucose, dextrin, soluble starch, sucrose, glycerol, etc. ; the nitrogen source includes e.g. an ammonium salt, peptone, casein, etc.; and the inorganic substance includes e.g. calcium chloride, sodium dihydrogenphosphate, magnesium chloride, etc. A yeast extract, vitamins, etc. may further be added. The pH of the medium is preferably about 5 to 8. To culture the microorganism of the genus Escherichia, the medium is preferably Terrific broth (K. D. Tartof et al.: Bethesda Res. Lab. Focus, 9, 12 (1987)) or the like. The transformant is cultured usually at about 15 to 43° C. for about 8 to 24 hours, if necessary under aeration or stirring. After the culture is finished, the recombinant DNA containing DNA coding for smooth muscle-type myosin heavy chain SM1 isoform protein can be obtained through purification by the Birnboim method (Nucleic Acid Res., 7, 1513 (1979)), etc.

To culture the transformant from animal cells as the host, the medium used includes a medium containing about 5 to 20% fetal bovine serum, such as 199 medium (Morgan et al.: Proc. Soci. Biol. Med., 73, 1 (1950)), MEM medium (H. Eagle: Science, 122, 501 (1952)), DMEM (R. Dulbecco et al.: Virology, 8, 396 (1959)) or the like. The pH is preferably in the range of about 6 to 8. The transformant is cultured usually at about 30 to 40° C. for about 18 to 60 hours, if necessary under aeration or stirring.

Because virus particles containing the recombinant DNA are released into the culture supernatant, the recombinant DNA containing DNA coding for smooth muscle-type myosin heavy chain SM1 isoform protein can be obtained from the supernatant by concentrating and purifying virus particles by the cesium chloride centrifugation method (Koji Sawada et al.: "Shin Seikagaku Jikken Kouza 2-V" (New Biochemistry Experimental Course 2-V), 33 (1992)), the polyethylene glycol precipitation method (Arch. Virol., 71, 185 (1982)), the filter concentration method (J. Cell. Biol., 111, 217 (1990)), etc.

BEST MODE FOR CARRYING OUT THE INVENTION

Figure 1:
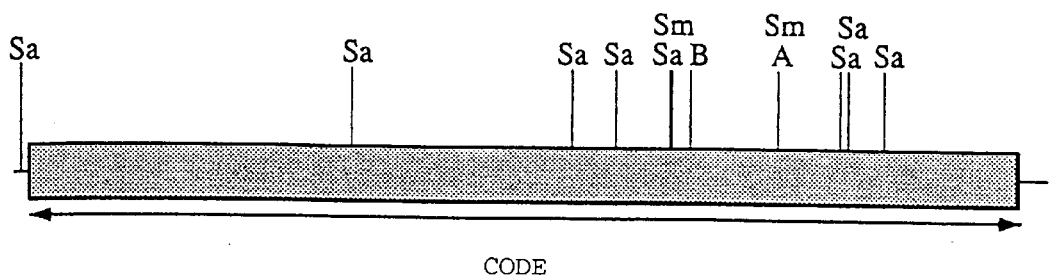
FIG. 1 shows a restriction enzyme map of the cDNA coding for mouse smooth muscle-type myosin heavy chain SM1 isoform protein and the location of the coding region.
Plasmid name: SM-1 F text
Plasmid size: 6175 bp
Region in the frame: coding region
A: ApaI
B: BamHI
Sa: SacI
Sm: SmaI

Hereinafter, the present invention is described in more detail with reference to Examples which however are not intended to limit the scope of the present invention.

EXAMPLE 1

Recombinant DNA Comprising DNA Coding for Mouse Smooth Muscle-type Myosin Heavy Chain SM1 Isoform Protein Inserted into Vector DNA (a) Preparation of a Probe Plasmids pSMHC29 and pIH61 in which a cDNA fragment coding for rabbit smooth muscle-type myosin heavy chain SM2 isoform protein had been cloned (J. Biol. Chem., 264, 9734–9737 (1989)) were used. These were digested with EcoRI (a product of Takara Shuzo Co., Ltd.; the restriction enzymes used hereinafter are products of Takara Shuzo Co., Ltd. unless otherwise specified) to prepare a cDNA fragment of rabbit smooth muscle-type myosin heavy chain SM2 isoform protein to be inserted. The cDNA fragment was labeled using an ECL direct DNA labeling system (Amersham) to be used as a probe in the following screening.

(b) Screening

A λ gtll vector mouse uterus cDNA library (Clontech) was mixed with E. coli Y1090 (Clontech) and incubated at 37° C. for 15 minutes, followed by adding 0.7% agarose NZY (Nucleic Acid Res., 16, 7583–7600 (1988)), and it was then spread on a 1.5% agar NZY plate. A nylon filter was placed on the plate wherein plaques occurred so that the plaques were transferred to the filter. This filter was subjected to denaturation by alkali treatment and the DNA was fixed by heating at 80° C. for 2 hours. The DNA was hybridized to the probe previously labeled according to the protocol of the ECL direct DNA labeling system in (a) above. Then, the hybridized clones were detected by autoradiography using an ECL detection system (Amersham).

(c) Analysis of DNA Nucleotide Sequence

Four clones were identified and each clone was subcloned in pUC119 (Takara Shuzo Co., Ltd.) or pBluescript SK(−) (Stratagene) for analysis of the DNA nucleotide sequence. E. coli DH5α was transformed with the resulting plasmids to give transformants Escherichia coli DH5α/pmsmhc20, pmsmhcC5, pmsmhcN08 and pmsmhcN14. The plasmids produced by the transformants were subjected to stepwise deletion by digestion with an exonuclease or to digestion with a suitable restriction enzyme, followed by self-cyclization or subcloning to prepare template DNA for sequence analysis (Gene, 28, 351–359 (1984)). A fluorescence type DNA sequencer (Applied Biosystems) was used for sequencing and MacMolly (Soft Gene GmbH) was used for data analysis. The nucleotide sequence thus determined is shown in SEQ ID NO:1. The amino acid sequence deduced from the nucleotide sequence is also shown in SEQ ID NO:1.

(d) Construction of an Expression Plasmid for Mouse Smooth Muscle-type Myosin Heavy Chain SM1 Isoform From the 4 clones previously obtained, plasmid pmSM1 containing cDNA coding for the whole coding region for SM1 isoform was prepared in the following manner (J. Sambrook et al., Molecular Cloning, 2nd Ed., Vol. 1, Cold Spring Harbor Laboratory Press, 1989). To shorten the 5'-non-coding region, plasmid pmsmhcN14 i.e. one of the 4 clones was digested with restriction enzymes BamHI and BglII and a 5-kb DNA fragment was purified and recovered therefrom. The DNA fragment was self-cyclized and transformed into E. coli DH5α to give an ampicillin resistant colony. From the colony, a desired microorganism is picked up and cultured, and plasmid DNA was recovered using a known method (H. C. Birnboim et al.: Nucleic Acid Res., 7, 1513 (1979)). The structure of the plasmid thus obtained was confirmed by agarose gel electrophoresis after digestion with BamHI and KpnI. The plasmid was designated pmsmhcN14'.

The resulting plasmid pmsmhcN14' was digested with restriction enzymes NsiI (New England Biolabs) and EcoRV, and a 4-kb DNA fragment was purified and recovered therefrom. Separately, plasmid pmsmhcN08 was also digested with NsiI and EcoRV, and a 1-kb DNA fragment was purified, recovered and ligated into the previously obtained 4-kb DNA fragment derived from plasmid pmsmhcN14', whereby plasmid pmsmhcN14-08 was constructed. The structure of this plasmid was confirmed by digestion with NsiI and EcoRV. The resulting plasmid pmsmhcN14-08 was digested with restriction enzymes ApaI and KpnI and a 5-kb DNA fragment was purified and recovered therefrom. Plasmid pmsmhc20 was also digested in a similar manner with ApaI and KpnI, and a 1.5-kb DNA fragment was purified, recovered and ligated into the previously obtained 5-kb DNA fragment, whereby plasmid pmsmhcNl4-08-20 was constructed. The structure of the plasmid was confirmed by digestion with ApaI and KpnI.

The resulting plasmid pmsmhcN14-08-20 was digested with restriction enzyme ApaI and a 6-kb DNA fragment was purified and recovered therefrom. Plasmid pmsmhcC5 was also digested with ApaI, and a 2-kb DNA fragment was purified, recovered and ligated into the 6-kb DNA fragment from pmsmhcN14-08-20 whereby plasmid pmsmhcN14-08-5-20 was constructed. The structure of this plasmid was confirmed by digestion with EcORI and NruI.

Plasmid pmsmhcN14-08-5-20 was digested with restriction enzymes NsiI and NruI and a 8-kb DNA fragment was purified and recovered therefrom. Plasmid pmsmhcN08 was also digested in a similar manner with NsiI and NruI, and a 1.5-kb DNA fragment was purified, recovered and ligated into the previously obtained 8-kb DNA fragment, whereby plasmid pmSM1 containing the whole coding region for mouse smooth muscle-type myosin heavy chain SM1 isoform was constructed. The structure of this plasmid was confirmed by digestion with NsiI and NruI.

The resulting plasmid pmSM1 was digested with restriction enzymes XbaI and KpnI and a 6-kb DNA fragment was purified and recovered therefrom. Separately, expression vector PAGE208 derived from expression vector PAGE207 (Japanese Patent Laid-Open Publication No. 46841/1994) by deleting an SmaI site located in a promoter region for hygromycin B resistance gene in PAGE207 was digested with XbaI and KpnI, and a 6-kb DNA fragment was purified, recovered, and ligated into the previously obtained 6-kb DNA fragment derived from plasmid pmSM1, whereby expression plasmid pSE-SM1-Hyg was constructed. The structure of the plasmid was confirmed by digestion with XbaI and KpnI.

A DNA fragment obtained by digestion of plasmid pmSM1 with XbaI and KpnI was blunt-ended with a DNA blunting kit (Takara Shuzo Co., Ltd.). Separately, expression vector pCXN2 was digested with XhoI and blunt-ended with the DNA blunting kit (Takara Shuzo Co., Ltd.). These 2 kinds of DNA were ligated to construct expression plasmid pCAG-SM1. The structure of the plasmid was confirmed by digestion with BglII.

The above plasmid pSE-SM1-Hyg was inserted into *Escherichia coli* whereby a transformant was obtained.

The transformant has been deposited as *Escherichia coli* pSE-SM1-Hyg (FERM BP-4974) with the National Institute of Bioscience and Human-Technology, Agency of Industrial Science and Technology, 1–3, Higashi 1 chome, Tsukuba-shi, Ibaraki-ken, Japan, since Jan. 24, 1995.

EXAMPLE 2

Figure 2:
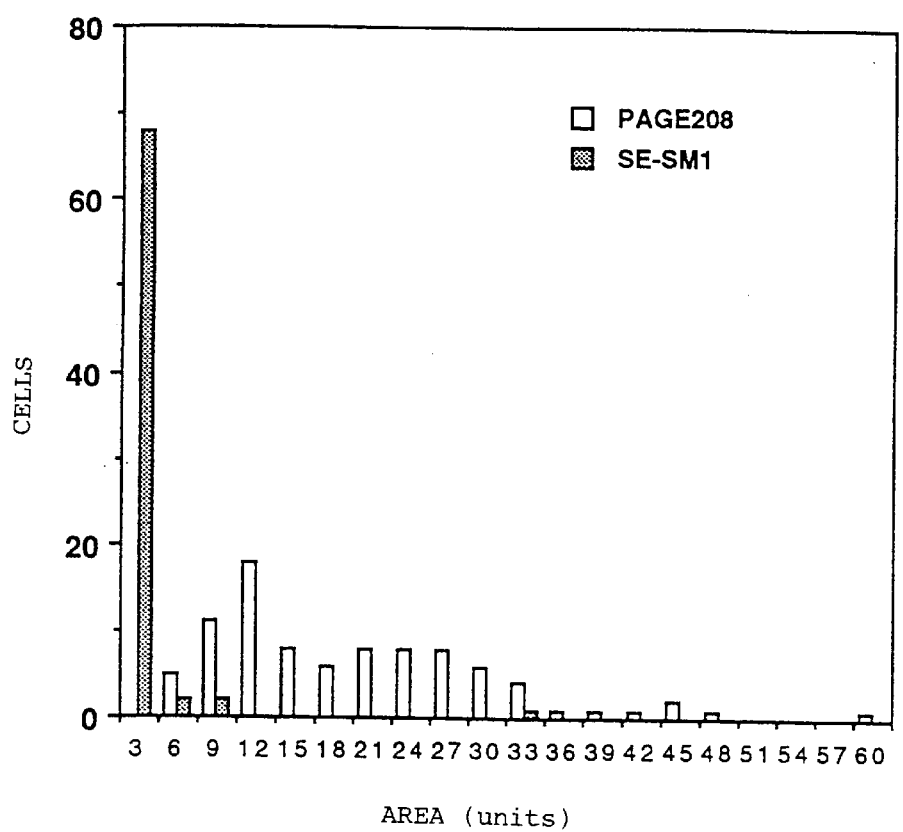
FIG. 2 shows the area of CHO cell colonies selected with hygromycin after introduction of plasmid pSE-SM1-Hyg vs. the area of CHO cell colonies after introduction of plasmid PAGE208.
Figure 3:
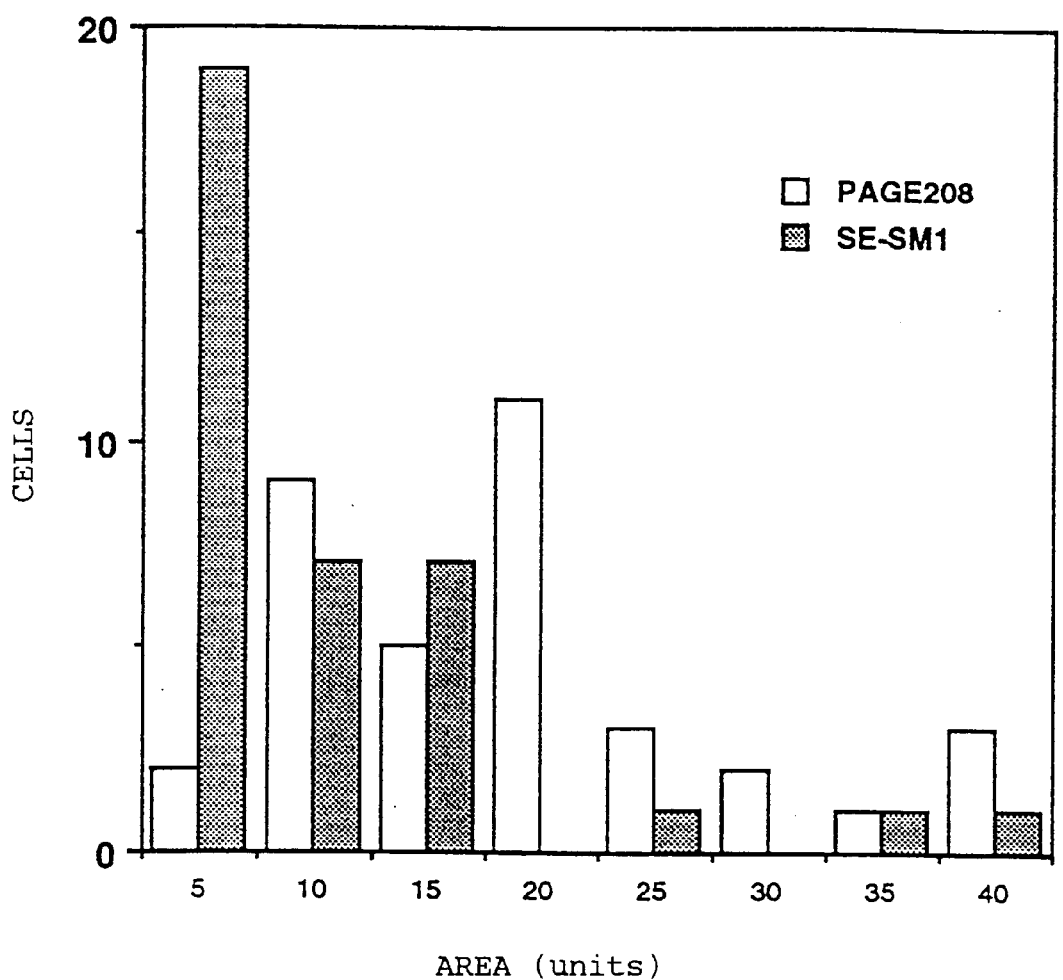
FIG. 3 shows the area of HeLa cell colonies selected with hygromycin after introduction of plasmid pSE-SM1-Hyg vs. the area of HeLa cell colonies after introduction of plasmid PAGE208.
Figure 4:
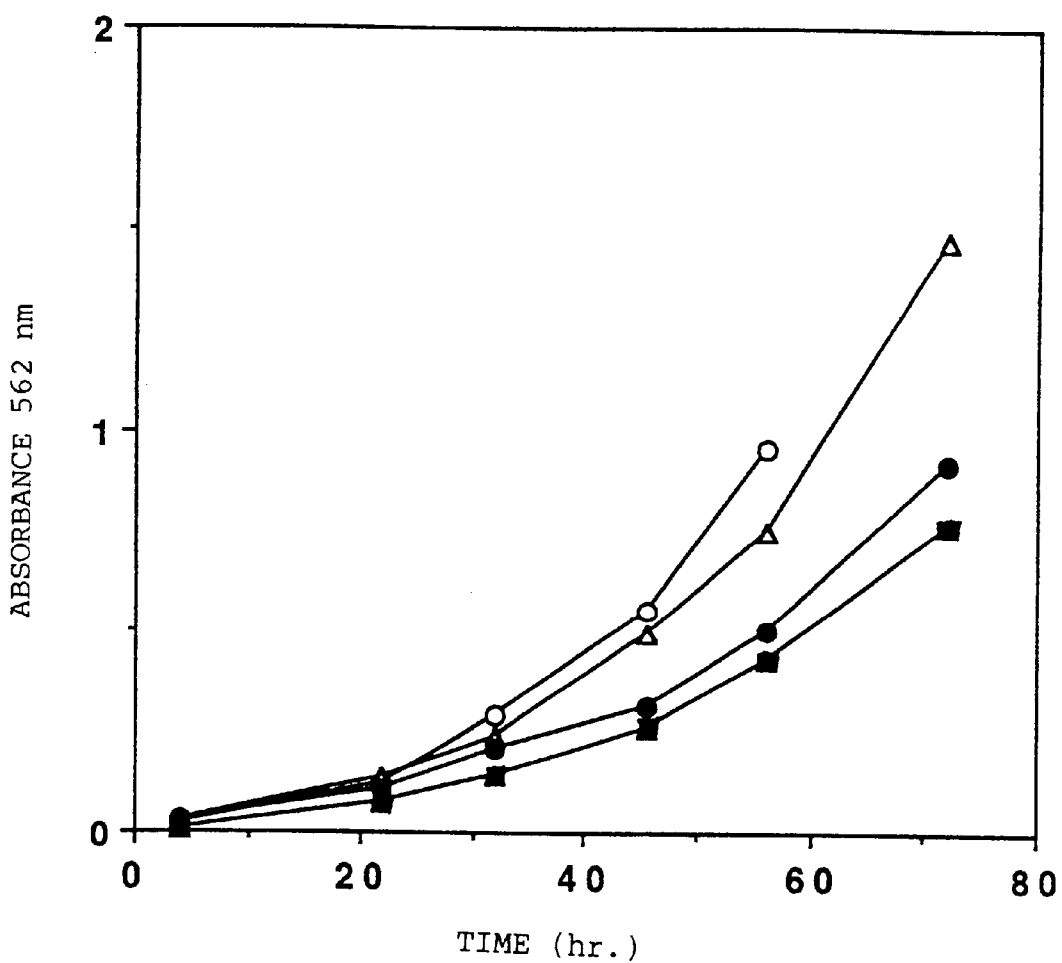
FIG. 4 shows the comparison among the proliferation rates of the wild type, the PAGE208-introduced clone and the SM1 isoform-expressing clones (SM1-5-2-1, SM1-5-3-3) of CHO cells by the MTT method.
—○— CHO
—△— PAGE208-1
—●— SM1 5-2-1
—■— SM1 5-3-3

Effect of Expression of SM1 Isoform in CHO Cells and HeLa Cells on Cell Proliferation 2 µg of expression plasmid pSE-SM1-Hyg and 4 µl of lipofectamine™ (Gibco) were mixed and incubated for 15 minutes to produce a complex. The complex was added to CHO cells or HeLa cells and incubated at 37° C. for 5 hours so that the gene was introduced into the cells. The cells were diluted and spread on a vessel, and cells into which the gene had been introduced were selected in the presence of hygromycine™ (Sigma). About 10 days later, the drug resistant cell colonies were stained with Coomassie Blue™ (Bio-Rad) and their area was measured with an image analyzer. As a result, many of the colonies had smaller areas than those of the colonies carrying the introduced control vector PAGE208, indicating that their proliferation was inhibited by the expression of the SM1 isoform (FIGS. 2 and 3). Separately, the hygromycin resistant CHO cells were cloned and the resulting clones SM1-5-2-1 and SM1-5-3-3 were examined for their proliferation rate. The result indicated that their proliferation rate was lower than that of the wild-type or PAGE208-introduced cells (FIG. 4).

EXAMPLE 3

Inhibitory Effect of Forcible Introduction of SM1 Gene into Vessel Walls in a Balloon Injured Rabbit Model on Thickening of the Intima A PTCA catheter at 3 French (Fr) was inserted under X-raying through the femoral artery into the right common carotid artery of a Japanese white domestic rabbit weighing 2.4 to 3.2 kg. The right common carotid artery was abraded 3 times with a balloon expanded at 10 atm. to injure the vessel wall. Three days after the abrasion, the injured portion of the vessel was infused with a mixture of 300 mg pCAG-SM1 and lipofectin (Gibco BRL) through a Wolinsky type infusion catheter (a product of BARD) at 6 atm. For Comparative Example, other domestic rabbits were treated in the same manner, and in place of pCAG-SM1, an expression vector for β-galactosidase was introduced into the injured portion of the vessel.

Three days after the infusion, the animals were sacrificed by perfusion with heparin physiological saline and their right common carotid arteries were removed and cut thin, followed by adding 1 ml ISOGEN (Wako Pure Chemical Industries, Ltd.), and the tissues were homogenized with a Polytron homogenizer. The whole RNA was extracted by the AGPC method (P. Chomczynski and N. Sacchi: Anal. Biochem., 162, 156–159 (1987)), and the MRNA for SM1 was amplified by the RT-PCR method. The amplified DNAs from the Example (introduction of SM1 gene) and Comparative Example (introduction of β-galactosidase gene) and their fragments digested with restriction enzyme NheI were subjected to agarose gel electrophoresis. The SM1 band was detected strongly in the Example and faintly in the Comparative Example, and the band in only the Example was digested with NheI. The supported that the SM1 gene derived from the mouse was expressed in the Example because the digestion site of the restriction enzyme is not present in the DNA for SM1 derived from the domestic rabbit but present in the mouse SM1.

Figure 5:
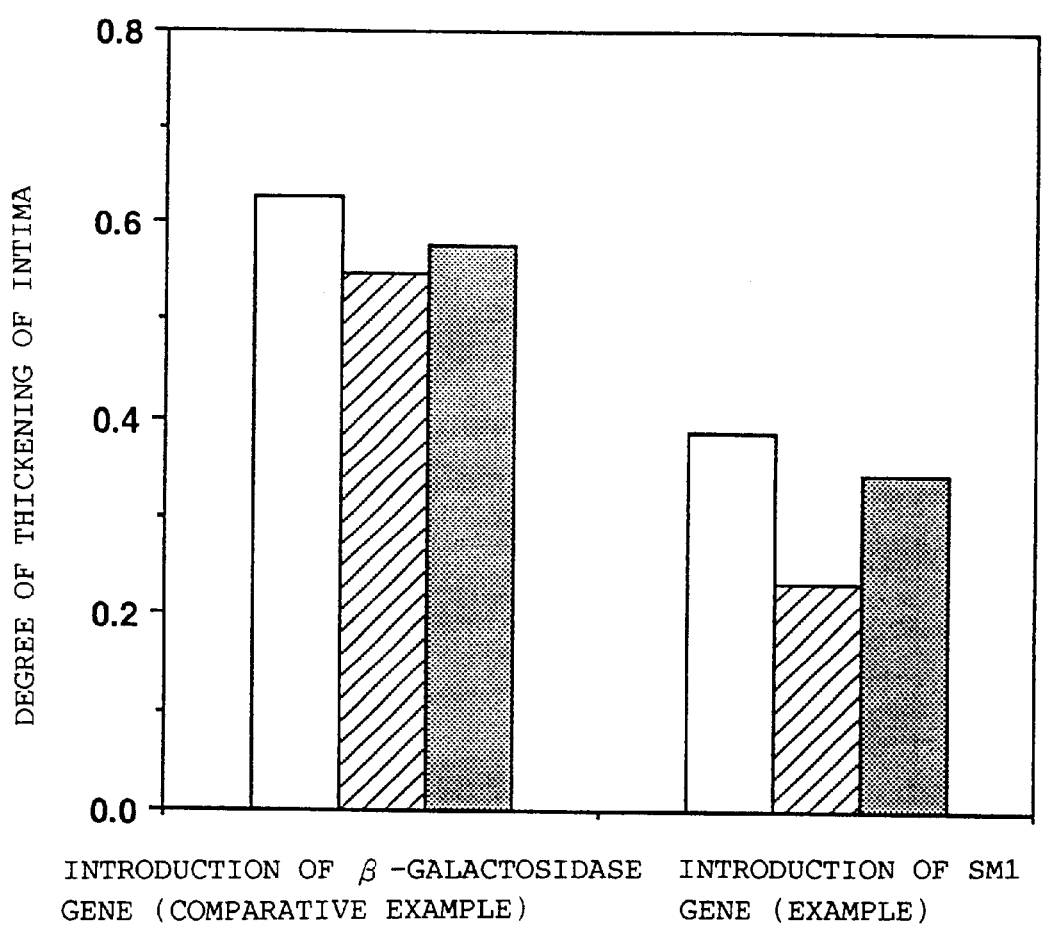
FIG. 5 shows the degrees of thickening of the intima after introduction of the SM1 gene (Example) and β-galactosidase gene (Comparative Example) into the vessel walls in a balloon injured rabbit model.

Two weeks after introduction of the gene, the rabbits were sacrificed by perfusion with PBS containing 2% paraformaldehyde and fixed, and their right common carotid arteries were removed. The part into which the infusion catheter had been introduced was dissected out and embedded in paraffin, and a thin round section of the vessel was prepared. One vessel was divided equally into 4 tissues and 1 section was prepared from each tissue and stained with hematoxylin-eosin. The vessel was divided along the internal elastic plate as the boundary into the intima and media, and the area of each was determined. The intima area/media area ratio was determined for each section and the mean was determined. The degree of thickening of the intima was determined using the mean. From the degree of thickening of the intima as determined for 3 animals in the Example and 3 animals in the Comparative Example, it was confirmed that thickening of the intima was inhibited by forcible introduction of the SM1 gene (FIG. 5).

The results suggested that plasmids pSE-SM1-Hyg and pCAG-SM1 possess the effect of depressing cell proliferation and are effective in restenosis of arteriosclerosis, caused by abnormal proliferation of vascular cells.

INDUSTRIAL APPLICABILITY

It was revealed that the proliferation of animal cells is inhibited when the recombinant DNA comprising DNA coding for smooth muscle-type myosin heavy chain SM1 isoform protein inserted into vector DNA according to the present invention is expressed in the animal cells. The effect was also observed in human-derived HeLa cells. Therefore, the recombinant DNA of the present invention can be used effectively as an agent for gene therapy of restenosis after PTCA treatment.

What is claimed is:

1. An isolated DNA encoding smooth muscle-type myosin heavy chain SM1 isoform protein as set forth in SEQ ID NO:3.

2. The DNA of claim 1, wherein said DNA consists of nucleotides 105 to 6020 of SEQ ID NO: 1.

3. A vector containing the DNA of claim 1.

4. The vector of claim 3, further comprising a promoter operably linked to the DNA.

5. The vector of claim 3, wherein said vector is a plasmid.

6. The vector of claim 5, wherein said plasmid is pSE-SM1-Hyg.

7. The vector of claim 3, wherein said vector is a viral vector.

8. The vector of claim 7, wherein said viral vector is a retrovirus vector or an adenovirus vector.

9. A cultured host cell comprising the vector of claim 3.

10. The host cell of claim 9, wherein said cultured host cell is a microorganism.

11. The host cell of claim 9, wherein said cultured host cell is an animal cell.

12. A pharmaceutical composition comprising the vector of claim 3 and a pharmaceutically acceptable carrier.

13. A method of inhibiting vascular smooth muscle cell proliferation following angioplasty comprising administering a therapeutically effective amount of a vector comprising a DNA sequence encoding myosin heavy chain SM1 isoform polypeptide that inhibits vascular smooth muscle cell proliferation, wherein the vector is administered to a patient by using an infusion catheter so the vector is at or near the site of angioplasty.

14. A method of treating restenosis following angioplasty comprising administering a therapeutically effective amount of a vector comprising a DNA sequence encoding myosin heavy chain SM1 isoform polypeptide that treats restenosis, wherein the vector is administered to a patient by using an infusion catheter so the vector is at or near the site of angioplasty.

15. The method of claim 13, wherein the myosin heavy chain SM1 isoform polypeptide comprises SEQ ID NO:3.

16. The method of claim 14, wherein the myosin heavy chain SM1 isoform polypeptide comprises SEQ ID NO:3.

* * * * *

SEQUENCE LISTING

```
<160> NUMBER OF SEQ ID NOS: 5

<210> SEQ ID NO 1
<211> LENGTH: 6175
<212> TYPE: DNA
<213> ORGANISM: Mus musculus
<220> FEATURE:
<221> NAME/KEY: CDS
<222> LOCATION: (105)...(6020)

<400> SEQUENCE: 1
agatttggac catcccagcc tgggatcagt gccagatccg agctctccat ccggtgtcct        60
cctgctaatc caccccgga gtagatctgg gaccaccaga catc atg gcg cag aaa       116
                                              Met Ala Gln Lys
                                                1 ggg cag ctc agc gat gat gag aag ttc ctc ttt gtg gat aaa aac ttc       164
Gly Gln Leu Ser Asp Asp Glu Lys Phe Leu Phe Val Asp Lys Asn Phe
  5                  10                  15                  20 atg aac agc cca atg gct cag gcc gac tgg gta gcc aag aag ctg gtg       212
Met Asn Ser Pro Met Ala Gln Ala Asp Trp Val Ala Lys Lys Leu Val
                 25                  30                  35 tgg gtc cct tca gag aag cag ggc ttc gaa gca gcc agc atc aag gag       260
Trp Val Pro Ser Glu Lys Gln Gly Phe Glu Ala Ala Ser Ile Lys Glu
             40                  45                  50 gag aag ggc gat gag gtg gtc gtg gag ttg gtg gaa aat gga aag aag       308
Glu Lys Gly Asp Glu Val Val Val Glu Leu Val Glu Asn Gly Lys Lys
         55                  60                  65 gtc aca gtt ggc aaa gat gac atc caa aaa atg aac cca ccc aag ttc       356
Val Thr Val Gly Lys Asp Asp Ile Gln Lys Met Asn Pro Pro Lys Phe
     70                  75                  80 tct aag gtg gag gac atg gca gag ctg acg tgc ctc aat gag gcc tct       404
Ser Lys Val Glu Asp Met Ala Glu Leu Thr Cys Leu Asn Glu Ala Ser
 85                  90                  95                 100 gtg ctg cac aac ctg agg gag cga tac ttc tca ggc ctc atc tat acc       452
Val Leu His Asn Leu Arg Glu Arg Tyr Phe Ser Gly Leu Ile Tyr Thr
                105                 110                 115 tac tct ggc ctc ttc tgt gtg gtg gtc aac ccc tac aag tac cta ccc       500
Tyr Ser Gly Leu Phe Cys Val Val Val Asn Pro Tyr Lys Tyr Leu Pro
            120                 125                 130 atc tac tca gaa aag atc gtg gat atg tac aag ggc aag aag agg cat       548
Ile Tyr Ser Glu Lys Ile Val Asp Met Tyr Lys Gly Lys Lys Arg His
        135                 140                 145
```

-continued

```
gag atg ccg cct cac atc tat gcc att gcc gac aca gcc tac aga agc    596
Glu Met Pro Pro His Ile Tyr Ala Ile Ala Asp Thr Ala Tyr Arg Ser
    150                 155                 160 atg cta caa gat cgt gaa gac cag tcc att ctg tgc aca ggt gag tct    644
Met Leu Gln Asp Arg Glu Asp Gln Ser Ile Leu Cys Thr Gly Glu Ser
165                 170                 175                 180 gga gcc gga aag aca gag aac aca cag aaa gtc ata cag tac ttg gct    692
Gly Ala Gly Lys Thr Glu Asn Thr Gln Lys Val Ile Gln Tyr Leu Ala
                185                 190                 195 gtg gtg gcg tcc tcc cac aag ggc aag aaa gac agc agc atc acg ggg    740
Val Val Ala Ser Ser His Lys Gly Lys Lys Asp Ser Ser Ile Thr Gly
            200                 205                 210 gag ctg gaa aag cag ctt cta cag gca aac cca atc ctg gag gct ttc    788
Glu Leu Glu Lys Gln Leu Leu Gln Ala Asn Pro Ile Leu Glu Ala Phe
        215                 220                 225 ggc aat gcg aaa acc gtc aag aac gac aac tcc tct cgc ttt ggc aag    836
Gly Asn Ala Lys Thr Val Lys Asn Asp Asn Ser Ser Arg Phe Gly Lys
    230                 235                 240 ttc att cgc atc aac ttc gat gtc act ggt tac att gta ggt gcc aat    884
Phe Ile Arg Ile Asn Phe Asp Val Thr Gly Tyr Ile Val Gly Ala Asn
245                 250                 255                 260 att gaa aca tat ctt ctg gaa aag tct agg gct att cga cag gct agg    932
Ile Glu Thr Tyr Leu Leu Glu Lys Ser Arg Ala Ile Arg Gln Ala Arg
                265                 270                 275 gat gag aga aca ttt cac atc ttc tac tac ctg ctc gcc gga gcc aag    980
Asp Glu Arg Thr Phe His Ile Phe Tyr Tyr Leu Leu Ala Gly Ala Lys
            280                 285                 290 gaa aag atg aaa agt gac ctg ctt ttg gag agc ttc aac agc tac aca   1028
Glu Lys Met Lys Ser Asp Leu Leu Leu Glu Ser Phe Asn Ser Tyr Thr
        295                 300                 305 ttt tta tcc aat ggc ttt gtg ccc atc cca gct gca caa gat gat gag   1076
Phe Leu Ser Asn Gly Phe Val Pro Ile Pro Ala Ala Gln Asp Asp Glu
    310                 315                 320 atg ttc cag gag aca ctg gaa gcc atg tct atc atg ggc ttc aat gaa   1124
Met Phe Gln Glu Thr Leu Glu Ala Met Ser Ile Met Gly Phe Asn Glu
325                 330                 335                 340 gag gaa cag cta gcc atc ttg aag gta gta tca tct gtc ctt cag ctt   1172
Glu Glu Gln Leu Ala Ile Leu Lys Val Val Ser Ser Val Leu Gln Leu
                345                 350                 355 gga aac att gtc ttc aag aag gag cga aac aca gac cag gca tcc atg   1220
Gly Asn Ile Val Phe Lys Lys Glu Arg Asn Thr Asp Gln Ala Ser Met
            360                 365                 370 cct gat aac aca gcg gct cag aaa gtt tgc cac ctc gtg ggg att aat   1268
Pro Asp Asn Thr Ala Ala Gln Lys Val Cys His Leu Val Gly Ile Asn
        375                 380                 385 gtg aca gat ttc act aga gcc atc ctg acc cca cgt atc aaa gtt gga   1316
Val Thr Asp Phe Thr Arg Ala Ile Leu Thr Pro Arg Ile Lys Val Gly
    390                 395                 400 cgg gat gtg gtg cag aag gct cag acc aaa gaa cag gct gac ttc gcc   1364
Arg Asp Val Val Gln Lys Ala Gln Thr Lys Glu Gln Ala Asp Phe Ala
405                 410                 415                 420 atc gag gcc tta gcc aag gcc acc tat gag cgc ctt ttc cga tgg att   1412
Ile Glu Ala Leu Ala Lys Ala Thr Tyr Glu Arg Leu Phe Arg Trp Ile
                425                 430                 435 ctc agc cgt gta aac aag gcc ttg gac aag acc cat cgg cag ggg gcc   1460
Leu Ser Arg Val Asn Lys Ala Leu Asp Lys Thr His Arg Gln Gly Ala
            440                 445                 450 tcc ttc ctg ggc att ctg gat att gct ggg ttt gaa atc ttt gag gta   1508
Ser Phe Leu Gly Ile Leu Asp Ile Ala Gly Phe Glu Ile Phe Glu Val
```

-continued

| | | | |
|---|---|---|---|
| | 455 | 460 | 465 |

| | | |
|---|---|---|
| aac tcc ttc gag cag ctg tgc atc aac tac acc aac gag aag ctg cag<br>Asn Ser Phe Glu Gln Leu Cys Ile Asn Tyr Thr Asn Glu Lys Leu Gln<br>    470                            475                            480 | 1556 |
| cag ctg ttc aac cac acg atg ttc atc ctg gag cag gaa gag tac cag<br>Gln Leu Phe Asn His Thr Met Phe Ile Leu Glu Gln Glu Glu Tyr Gln<br>485                              490                            495                            500 | 1604 |
| cga gag ggc atc gag tgg aac ttc atc gac ttc ggc ctg gac ctg cag<br>Arg Glu Gly Ile Glu Trp Asn Phe Ile Asp Phe Gly Leu Asp Leu Gln<br>                                          505                            510                            515 | 1652 |
| cct agt att gag ctg att gag cgg ccg aac aac cct ccc ggt gtg ctg<br>Pro Ser Ile Glu Leu Ile Glu Arg Pro Asn Asn Pro Pro Gly Val Leu<br>                    520                            525                            530 | 1700 |
| gcc ctg ctg gat gaa gaa tgc tgg ttc ccc aaa gct aca gac aag tct<br>Ala Leu Leu Asp Glu Glu Cys Trp Phe Pro Lys Ala Thr Asp Lys Ser<br>                  535                            540                            545 | 1748 |
| ttt gtg gag aag cta tgc tca gag cag gga aat cac ccc aaa ttt cag<br>Phe Val Glu Lys Leu Cys Ser Glu Gln Gly Asn His Pro Lys Phe Gln<br>          550                            555                            560 | 1796 |
| aag ccc aag cag cta aag gac aaa aca gag ttc tcc atc atc cac tat<br>Lys Pro Lys Gln Leu Lys Asp Lys Thr Glu Phe Ser Ile Ile His Tyr<br>565                            570                            575                            580 | 1844 |
| gct ggg aag gtg gac tac aat gca agt gcc tgg ctg acc aag aac atg<br>Ala Gly Lys Val Asp Tyr Asn Ala Ser Ala Trp Leu Thr Lys Asn Met<br>                                        585                            590                            595 | 1892 |
| gac ccg cta aat gac aat gtg aca tca ctc ctc aat gcc tcc tct gac<br>Asp Pro Leu Asn Asp Asn Val Thr Ser Leu Leu Asn Ala Ser Ser Asp<br>                  600                            605                            610 | 1940 |
| aag ttt gtg gct gac ctg tgg aag gat gtg gac cgc att gtg ggg ctg<br>Lys Phe Val Ala Asp Leu Trp Lys Asp Val Asp Arg Ile Val Gly Leu<br>                  615                            620                            625 | 1988 |
| gac cag atg gcc aag atg act gag agc tca ctg ccc agt gcc tca aag<br>Asp Gln Met Ala Lys Met Thr Glu Ser Ser Leu Pro Ser Ala Ser Lys<br>          630                            635                            640 | 2036 |
| acc aaa aag ggc atg ttc cgc acc gtg gga cag ctc tac aaa gag cag<br>Thr Lys Lys Gly Met Phe Arg Thr Val Gly Gln Leu Tyr Lys Glu Gln<br>645                          650                            655                            660 | 2084 |
| ttg ggg aaa ctg atg gct aca ctg cgc aat acc acg gct aac ttt gtg<br>Leu Gly Lys Leu Met Ala Thr Leu Arg Asn Thr Thr Ala Asn Phe Val<br>                    665                            670                            675 | 2132 |
| cgc tgc atc atc ccc aac cat gag aag agg tct ggc aag ctg gat gca<br>Arg Cys Ile Ile Pro Asn His Glu Lys Arg Ser Gly Lys Leu Asp Ala<br>                  680                            685                            690 | 2180 |
| ttt cta gtg ctg gaa cag ctg cgc tgc aac ggt gtg ttg gaa ggc atc<br>Phe Leu Val Leu Glu Gln Leu Arg Cys Asn Gly Val Leu Glu Gly Ile<br>          695                            700                            705 | 2228 |
| cgc atc tgc cgt cag ggc ttc ccc aac agg att gtc ttc caa gag ttc<br>Arg Ile Cys Arg Gln Gly Phe Pro Asn Arg Ile Val Phe Gln Glu Phe<br>                  710                            715                            720 | 2276 |
| cgg caa cgc tat gag atc ctg gca gcg aac gcc atc ccc aaa ggc ttc<br>Arg Gln Arg Tyr Glu Ile Leu Ala Ala Asn Ala Ile Pro Lys Gly Phe<br>725                          730                            735                            740 | 2324 |
| atg gat gga aag caa gcc tgc att ctc atg atc aaa gcc ctc gaa ctt<br>Met Asp Gly Lys Gln Ala Cys Ile Leu Met Ile Lys Ala Leu Glu Leu<br>                  745                            750                            755 | 2372 |
| gac cct aac ctg tac agg att ggg cag agc aaa atc ttc ttc cga acg<br>Asp Pro Asn Leu Tyr Arg Ile Gly Gln Ser Lys Ile Phe Phe Arg Thr<br>                      760                            765                            770 | 2420 |
| ggg gtc ctg gcc cac cta gag gag gaa cga gac ctg aaa att act gat | 2468 |

-continued

```
                Gly Val Leu Ala His Leu Glu Glu Arg Asp Leu Lys Ile Thr Asp
                            775                 780                 785 gtc atc atg gcc ttc cag gca atg tgt cgt ggc tac ctt gcc aga aag          2516
Val Ile Met Ala Phe Gln Ala Met Cys Arg Gly Tyr Leu Ala Arg Lys
    790                 795                 800 gcc ttc acc aag agg cag caa cag ctg aca gcc atg aag gtg atc cag          2564
Ala Phe Thr Lys Arg Gln Gln Gln Leu Thr Ala Met Lys Val Ile Gln
805                 810                 815                 820 agg aac tgc gct gcc tac ctt aag ctc cgc aac tgg caa tgg tgg cgg          2612
Arg Asn Cys Ala Ala Tyr Leu Lys Leu Arg Asn Trp Gln Trp Trp Arg
                825                 830                 835 ctc ttc acc aaa gta aag cca ttg ctc cag gtg aca cgg cag gag gag          2660
Leu Phe Thr Lys Val Lys Pro Leu Leu Gln Val Thr Arg Gln Glu Glu
            840                 845                 850 gag atg cag gcc aag gag gag gag atg caa aag atc acg gag cgg cag          2708
Glu Met Gln Ala Lys Glu Glu Glu Met Gln Lys Ile Thr Glu Arg Gln
        855                 860                 865 cag aag gca gag act gag ttg aag gag ctg gag cag aag cac act cag          2756
Gln Lys Ala Glu Thr Glu Leu Lys Glu Leu Glu Gln Lys His Thr Gln
    870                 875                 880 ctg gct gag gag aag act ctg ctg cag gag cag ttg cag gca gag aca          2804
Leu Ala Glu Glu Lys Thr Leu Leu Gln Glu Gln Leu Gln Ala Glu Thr
885                 890                 895                 900 gag ctg tat gct gag tct gag gag atg cgg gtc cgg ttg gca gcc aag          2852
Glu Leu Tyr Ala Glu Ser Glu Glu Met Arg Val Arg Leu Ala Ala Lys
                905                 910                 915 aag cag gaa ctg gag gag atc cta cat gag atg gag gcc cgc ctg gag          2900
Lys Gln Glu Leu Glu Glu Ile Leu His Glu Met Glu Ala Arg Leu Glu
            920                 925                 930 gaa gag gaa gac cgg cgc cag caa cta cag gct gag agg aag aag atg          2948
Glu Glu Glu Asp Arg Arg Gln Gln Leu Gln Ala Glu Arg Lys Lys Met
        935                 940                 945 gct cag cag atg cta gac ctg gag gag caa ctg gag gag gaa gag gcc          2996
Ala Gln Gln Met Leu Asp Leu Glu Glu Gln Leu Glu Glu Glu Glu Ala
    950                 955                 960 gcc aga cag aaa cta cag cta gag aag gtc acg gct gag gcc aag atc          3044
Ala Arg Gln Lys Leu Gln Leu Glu Lys Val Thr Ala Glu Ala Lys Ile
965                 970                 975                 980 aag aaa ctg gag gat gac atc ttg gtt atg gat gat cag aac agt aaa          3092
Lys Lys Leu Glu Asp Asp Ile Leu Val Met Asp Asp Gln Asn Ser Lys
                985                 990                 995 ctt tca aaa gaa cga aaa ctc ctt gaa gag agg gtc agc gac ttg aca          3140
Leu Ser Lys Glu Arg Lys Leu Leu Glu Glu Arg Val Ser Asp Leu Thr
            1000                1005                1010 acc aac cta gca gaa gag gaa gaa aag gct aaa aac ctc aca aag ctg          3188
Thr Asn Leu Ala Glu Glu Glu Glu Lys Ala Lys Asn Leu Thr Lys Leu
        1015                1020                1025 aag agc aag cat gag tct atg atc tca gag ctg gag gtg agg ctg aag          3236
Lys Ser Lys His Glu Ser Met Ile Ser Glu Leu Glu Val Arg Leu Lys
    1030                1035                1040 aaa gag gag aag agc cgg cag gag ctg gag aaa ctc aag agg aaa ctg          3284
Lys Glu Glu Lys Ser Arg Gln Glu Leu Glu Lys Leu Lys Arg Lys Leu
1045                1050                1055                1060 gag ggt gat gcc agt gac ttc cat gag cag atc gct gac ttg cag gcc          3332
Glu Gly Asp Ala Ser Asp Phe His Glu Gln Ile Ala Asp Leu Gln Ala
                1065                1070                1075 cag att gca gag ctc aag atg cag ctg gca aag aaa gag gaa gag cta          3380
Gln Ile Ala Glu Leu Lys Met Gln Leu Ala Lys Lys Glu Glu Glu Leu
            1080                1085                1090
```

```
                                            -continued cag gca gct cta gcc agg ctt gat gaa gag atc gcc cag aaa aac aat    3428
Gln Ala Ala Leu Ala Arg Leu Asp Glu Glu Ile Ala Gln Lys Asn Asn
        1095                1100                1105 gcc cta aag aag att cgc gag cta gag ggc cat atc tca gac cta caa    3476
Ala Leu Lys Lys Ile Arg Glu Leu Glu Gly His Ile Ser Asp Leu Gln
    1110                1115                1120 gag gac cta gac tca gag cgg gct gcc agg aac aag gcc gag aag cag    3524
Glu Asp Leu Asp Ser Glu Arg Ala Ala Arg Asn Lys Ala Glu Lys Gln
1125                1130                1135                1140 aag cga gac ctg ggg gag gag ctg gag gca ctc aag acg gag ctg gag    3572
Lys Arg Asp Leu Gly Glu Glu Leu Glu Ala Leu Lys Thr Glu Leu Glu
                1145                1150                1155 gat acg ctg gac agc aca gct acc cag cag gag ctc aga gcc aag agg    3620
Asp Thr Leu Asp Ser Thr Ala Thr Gln Gln Glu Leu Arg Ala Lys Arg
1160                1165                1170 gaa cag gag gtg aca gtg ctg aag aag gcc ctg gat gag gag acg cgg    3668
Glu Gln Glu Val Thr Val Leu Lys Lys Ala Leu Asp Glu Glu Thr Arg
        1175                1180                1185 tcc cat gag gcc cag gtc cag gag atg agg cag aag cac aca cag gca    3716
Ser His Glu Ala Gln Val Gln Glu Met Arg Gln Lys His Thr Gln Ala
    1190                1195                1200 gtg gag gaa ctc aca gag cag ctg gag cag ttc aaa agg gcc aag gca    3764
Val Glu Glu Leu Thr Glu Gln Leu Glu Gln Phe Lys Arg Ala Lys Ala
1205                1210                1215                1220 aac ctg gac aaa agc aag cag aca ctg gag aag gag aac gcg gac ctg    3812
Asn Leu Asp Lys Ser Lys Gln Thr Leu Glu Lys Glu Asn Ala Asp Leu
                1225                1230                1235 gct ggg gag ctg cgt gtc ctg ggc cag gcg aag cag gag gtg gaa cac    3860
Ala Gly Glu Leu Arg Val Leu Gly Gln Ala Lys Gln Glu Val Glu His
1240                1245                1250 aag aag aag aag ctg gag gtg cag ctg cag gat ctg cag tcc aag tgc    3908
Lys Lys Lys Lys Leu Glu Val Gln Leu Gln Asp Leu Gln Ser Lys Cys
        1255                1260                1265 agt gat ggg gag cgt gcc cgg gct gag ctc agt gac aag gtc cac aag    3956
Ser Asp Gly Glu Arg Ala Arg Ala Glu Leu Ser Asp Lys Val His Lys
    1270                1275                1280 cta cag aat gaa gtg gag agt gtc act ggc atg ctc aat gag gca gag    4004
Leu Gln Asn Glu Val Glu Ser Val Thr Gly Met Leu Asn Glu Ala Glu
1285                1290                1295                1300 ggc aaa gcc atc aaa ctg gcc aaa gat gtg gct tcc ctt gga tcc cag    4052
Gly Lys Ala Ile Lys Leu Ala Lys Asp Val Ala Ser Leu Gly Ser Gln
                1305                1310                1315 ctt cag gac acc caa gag ctg ctc caa gaa gaa acc cgg cag aag ctc    4100
Leu Gln Asp Thr Gln Glu Leu Leu Gln Glu Glu Thr Arg Gln Lys Leu
1320                1325                1330 aat gtg tct acc aag ctg cgt cag ttg gaa gat gaa agg aac agc ctg    4148
Asn Val Ser Thr Lys Leu Arg Gln Leu Glu Asp Glu Arg Asn Ser Leu
        1335                1340                1345 cag gac cag ctg gat gag gag atg gag gct aag caa aac ctg gag cgc    4196
Gln Asp Gln Leu Asp Glu Glu Met Glu Ala Lys Gln Asn Leu Glu Arg
    1350                1355                1360 cat gtc tca aca ctg aac att cag ctc tca gac tct aag aag aag ctg    4244
His Val Ser Thr Leu Asn Ile Gln Leu Ser Asp Ser Lys Lys Lys Leu
1365                1370                1375                1380 cag gac ttt gca agt acc atc gag gtc atg gag gag ggg aag aag agg    4292
Gln Asp Phe Ala Ser Thr Ile Glu Val Met Glu Glu Gly Lys Lys Arg
                1385                1390                1395 tta cag aaa gag atg gag ggc ctc agc cag cag tat gag gag aag gcg    4340
Leu Gln Lys Glu Met Glu Gly Leu Ser Gln Gln Tyr Glu Glu Lys Ala
1400                1405                1410
```

```
gct gcc tat gac aaa ctg gag aaa acc aag aac agg ctc cag cag gag    4388
Ala Ala Tyr Asp Lys Leu Glu Lys Thr Lys Asn Arg Leu Gln Gln Glu
        1415                1420                1425 ctg gat gac ctg gtc gtg gac ttg gac aac cag cgg caa ctg gta tcc    4436
Leu Asp Asp Leu Val Val Asp Leu Asp Asn Gln Arg Gln Leu Val Ser
    1430                1435                1440 aat ctg gaa aag aag cag aag aaa ttt gac cag ttg tta gct gag gag    4484
Asn Leu Glu Lys Lys Gln Lys Lys Phe Asp Gln Leu Leu Ala Glu Glu
1445                1450                1455                1460 aag aac atc tcc tcc aag tat gcg gat gag aga gac cga gct gaa gca    4532
Lys Asn Ile Ser Ser Lys Tyr Ala Asp Glu Arg Asp Arg Ala Glu Ala
            1465                1470                1475 gag gcc agg gaa aag gag aca aag gct ttg tct cta gcc cgg gcc ctg    4580
Glu Ala Arg Glu Lys Glu Thr Lys Ala Leu Ser Leu Ala Arg Ala Leu
        1480                1485                1490 gag gaa gcc ctg gaa gcc aaa gaa gag ctg gag agg acc aac aag atg    4628
Glu Glu Ala Leu Glu Ala Lys Glu Glu Leu Glu Arg Thr Asn Lys Met
    1495                1500                1505 ctc aaa gct gag atg gaa gac ctg gtc agc tcc aag gat gat gta ggc    4676
Leu Lys Ala Glu Met Glu Asp Leu Val Ser Ser Lys Asp Asp Val Gly
1510                1515                1520 aag aac gtg cat gaa ctg gag aag tcc aag cgt gcc ttg gag acc cag    4724
Lys Asn Val His Glu Leu Glu Lys Ser Lys Arg Ala Leu Glu Thr Gln
1525                1530                1535                1540 atg gaa gag atg aaa acc cag ctg gag gag tcg gag gat gac gtg cag    4772
Met Glu Glu Met Lys Thr Gln Leu Glu Glu Ser Glu Asp Asp Val Gln
            1545                1550                1555 gcc act gag gat gcc aag ctg cgg cta gag gtc aac atg cag gcc ctc    4820
Ala Thr Glu Asp Ala Lys Leu Arg Leu Glu Val Asn Met Gln Ala Leu
        1560                1565                1570 aag ggc cag ttt gaa cgc gat ctc cag gct cgg gat gaa cag aat gag    4868
Lys Gly Gln Phe Glu Arg Asp Leu Gln Ala Arg Asp Glu Gln Asn Glu
    1575                1580                1585 gag aag agg agg cag cta cag cgg cag ctg cac gag tat gag aca gaa    4916
Glu Lys Arg Arg Gln Leu Gln Arg Gln Leu His Glu Tyr Glu Thr Glu
            1590                1595                1600 ctg gaa gat gaa cgg aag cag aga gct ctg gcg gcg gca gct aag aag    4964
Leu Glu Asp Glu Arg Lys Gln Arg Ala Leu Ala Ala Ala Ala Lys Lys
1605                1610                1615                1620 aag ctg gaa ggg gac cta aaa gac cta gag ctc cag gct gac tca gcc    5012
Lys Leu Glu Gly Asp Leu Lys Asp Leu Glu Leu Gln Ala Asp Ser Ala
            1625                1630                1635 atc aaa ggg agg gag gaa gcc atc aag cag ctt cga aaa ctg cag gct    5060
Ile Lys Gly Arg Glu Glu Ala Ile Lys Gln Leu Arg Lys Leu Gln Ala
        1640                1645                1650 cag atg aag gac ttc caa aga gag ctg gat gat gcc cgt gcc tcc agg    5108
Gln Met Lys Asp Phe Gln Arg Glu Leu Asp Asp Ala Arg Ala Ser Arg
    1655                1660                1665 gat gag atc ttt gcc acc tca aaa gag aat gag aag aaa gcc aag agt    5156
Asp Glu Ile Phe Ala Thr Ser Lys Glu Asn Glu Lys Lys Ala Lys Ser
        1670                1675                1680 ctg gag gca gac ctc atg cag ctc caa gag gac ctg gca gca gct gag    5204
Leu Glu Ala Asp Leu Met Gln Leu Gln Glu Asp Leu Ala Ala Ala Glu
1685                1690                1695                1700 aga gct cgc aag caa gct gac ctg gag aag gag gag ctg gcc gag gag    5252
Arg Ala Arg Lys Gln Ala Asp Leu Glu Lys Glu Glu Leu Ala Glu Glu
            1705                1710                1715 ctg gct agc agc ttg tca gga agg aat aca ctg cag gat gag aag cgc    5300
Leu Ala Ser Ser Leu Ser Gly Arg Asn Thr Leu Gln Asp Glu Lys Arg
```

-continued

```
                  1720               1725                1730
cgc ctg gag gca agg atc gcc caa cta gag gag gag ctg gag gaa gag     5348
Arg Leu Glu Ala Arg Ile Ala Gln Leu Glu Glu Glu Leu Glu Glu Glu
        1735               1740               1745 cag ggc aac atg gag gcc atg agt gat aga gta cgc aag gcc aca ctg     5396
Gln Gly Asn Met Glu Ala Met Ser Asp Arg Val Arg Lys Ala Thr Leu
    1750               1755               1760 cag gct gag caa ctg agc aat gag ctg gcc aca gaa cgc agc acg gct     5444
Gln Ala Glu Gln Leu Ser Asn Glu Leu Ala Thr Glu Arg Ser Thr Ala
1765               1770               1775               1780 cag aag aat gag agc gca cgg caa cag ctg gag cgc cag aac aag gaa     5492
Gln Lys Asn Glu Ser Ala Arg Gln Gln Leu Glu Arg Gln Asn Lys Glu
                1785               1790               1795 ctg cga agc aag ttg cag gag gta gaa ggt gct gtc aaa gcc aag ctc     5540
Leu Arg Ser Lys Leu Gln Glu Val Glu Gly Ala Val Lys Ala Lys Leu
        1800               1805               1810 aag tcc act gtt gcg gcg ctg gag gcc aag att gca cag ctg gag gag     5588
Lys Ser Thr Val Ala Ala Leu Glu Ala Lys Ile Ala Gln Leu Glu Glu
    1815               1820               1825 cag gtt gaa cag gag gcc aga gag aaa cag gcg gcc acc aag tcg ctg     5636
Gln Val Glu Gln Glu Ala Arg Glu Lys Gln Ala Ala Thr Lys Ser Leu
1830               1835               1840 aag caa aag gac aag aag cta aag gag gtc ctg ctg cag gtg gag gat     5684
Lys Gln Lys Asp Lys Lys Leu Lys Glu Val Leu Leu Gln Val Glu Asp
1845               1850               1855               1860 gag cgc aag atg gca gag cag tac aag gag cag gca gag aaa gga aac     5732
Glu Arg Lys Met Ala Glu Gln Tyr Lys Glu Gln Ala Glu Lys Gly Asn
                1865               1870               1875 acc aag gtc aag cag ctg aag agg cag ctg gaa gag gca gag gag gag     5780
Thr Lys Val Lys Gln Leu Lys Arg Gln Leu Glu Glu Ala Glu Glu Glu
        1880               1885               1890 tcc cag tgc atc aac gcc aac cgc agg aag ctg cag cgg gag cta gat     5828
Ser Gln Cys Ile Asn Ala Asn Arg Arg Lys Leu Gln Arg Glu Leu Asp
    1895               1900               1905 gag gcc aca gag agc aat gag gcc atg ggc cgt gag gtg aac gcc ctc     5876
Glu Ala Thr Glu Ser Asn Glu Ala Met Gly Arg Glu Val Asn Ala Leu
1910               1915               1920 aag agc aaa ctc agg aga gga aac gag gct tca ttt gtt cct tcc aga     5924
Lys Ser Lys Leu Arg Arg Gly Asn Glu Ala Ser Phe Val Pro Ser Arg
1925               1930               1935               1940 agg gct ggg ggc cgt aga gtt att gaa aac aca gat ggt tct gaa gaa     5972
Arg Ala Gly Gly Arg Arg Val Ile Glu Asn Thr Asp Gly Ser Glu Glu
                1945               1950               1955 gaa atg gac gct cgg gac tca gac ttc aat gga acc aaa gcc agt gaa     6020
Glu Met Asp Ala Arg Asp Ser Asp Phe Asn Gly Thr Lys Ala Ser Glu
        1960               1965               1970 taaattcagg attggacacc atgtcaggga aaacagaaca ctaaacgaca gcagagccca   6080
gcagactgct tagcacttgt gtccattcgt tctcaagtca cagaaatcac tccacccctc   6140
accaggagtc aaccacagcc ctgcacaaag ggtgt                              6175
```

<210> SEQ ID NO 2
<211> LENGTH: 5919
<212> TYPE: DNA
<213> ORGANISM: Mus musculus
<220> FEATURE:
<221> NAME/KEY: misc_feature
<222> LOCATION: (1)...(5919)
<223> OTHER INFORMATION: n = A,T,C or G

<400> SEQUENCE: 2

-continued

```
atggcgcaga anggncanct cagcgangat gagaagttcc tctttgtgga naanaacttc      60
atnaacagcc cnntggcnca ggccgactgg gtngccaaga ngctggtgtg ggtcccttcn     120
gagaagcagg gcttcgangc ncgccagcatc aaggaggaga agggngatga ggtggtcgtg    180
gagntggtgg anaatggnaa gaaggtcacn gtnggcaang atgacatcca naanatgaac    240
ccncccaagt tctcnaaggt ggangacatg gcngagctga cgtgbctcaa ngangcntcn    300
gtgctgcaca acctgaggga gvgntacttc tcnggnctca tctanacnta ctcnggcctc    360
ttctgbgtgg tggtcaaccc ctacaagyas ctncccatct actcnganaa gatcgtggan    420
atgtacaagg gcaagaagag gcangagatg ccnccncaca tctabgccat ngccgacacn    480
gcctacagna gcatgctnca ngatcgngan gaccagtcca ttctntgcac aggngagtct    540
ggagccggna agacngagaa cacnvagaaa gtcatncagt acntggcngt ggtggcntcn    600
tcccacaagg gcaagaanga cannagcatc acggggagc tgganaagca gcttctncan     660
gcaaacccna tcctggaggc nttnggcaan gcnaanacng tcaagaanga caactcctcn    720
cgnttnggca agttcatncg catcaacttn gangtcactg gttacatngt nggngccaan    780
attganacnt atctnctgga aaagtcnvgn gcnatncgnc angcnvgnga ngagagnacn    840
ttncacatct tntactacct gntngcnggn gccaaggana agatganaan tgacntgctn    900
ttggagngct tcaacancta cacattnntn tccaatggct ttgtgcccat cccagcngcn    960
cangatgang agatgttcca gganacnntg gangccatgt cnatcatggg cttcantgaa   1020
gaggancagc tnncnnttntt gaaggtngtn tcntcngtcc tncagcttgg aaacatngtc   1080
ttcaagaagg anvgaaacac agaccaggcn tccatgccng anaacacagc ngcncagaaa   1140
gtttgccacc tcntgggnat taangtgaca gatttcacna ganccatcct gaccccncgt   1200
atcaaagttg gacgggangt ngtgcagaan gctcagacna aagaacaggc ngacttcgcn   1260
ntcgaggcnt tngcnaaggc cacntatgan cgccttttcc gntggatnct cagccgtgtn   1320
aacaangccn tggacaagac ccatcggcag ggggcntcct tcctgggnat nctgganatn   1380
gctggntttg anatctttga ggtnaactcc ttcgagcagc tgtgcatcaa ctacaccaac   1440
gagaagctgc agcagctgtt caaccacacn atgttcatcc tggagcagga ngagtaccag   1500
cgngagggca tcgagtggaa cttcatcgac ttcggnctng acctgcagcc nwgyattgag   1560
ctnattgagc ggccgaacaa ccctccnggt gtgctggccc tgctggatga ngantgctgg   1620
ttccccaaag cnacaganaa gtcttttgtg gagaagctnt gcncagagca nggnaancac   1680 cccaantnc agaagcccaa gcagctnaag gacaaaacng agttctccat catccantan    1740
gctgggaagg tggactacaa ngcnagtgcc tggctgacca agaacatgga cccnctnaat   1800
gacaangtga cntcnctcct caangcctcc tcngacaagt tngtggcnga cctntggaag   1860
gangtggacc gcatngtggg gctggaccag atggccaaga tgacngagag ctcactgccc   1920
agngcctcna agaccaanaa gggcatgttc cgcacngtgg gncagctnta caangagcag   1980
ntggggaanc tgatgncac nctgcgcaan accacgncna acttngtgcg ctgcatcatc    2040
cccaaccang agaagnggtc nggcaagctg gangcnttnc tngtgctgga ncagctgcgn   2100
tgcaacgggg tgntgaagg catccgnatc tgccgncagg gcttccccaa caggatgntc    2160
ttccangagt tccgncaacg ctangagatc ctggcagcna acgccatccc caanggcttc   2220
atggatggna agcaagcctg cattctcatg atcaaagcnc tngaactnga cccnaacntg   2280
tacaggatng ggcagagcaa aatcttcttc cgnacgggng tnctggccca cctngaggag   2340
```

| | |
|---|---|
| gancgngacn tgaanatnac ngangtcatc atggccttcc aggcnatgtg tcgtggctac | 2400 |
| ctngccvgna aggccttcnc caagnggcag cancagctga cngccatgaa ggtgatccag | 2460 |
| aggaactgcg cngcctacct naagctncgn aactggcant ggtggcgnct cttcaccaan | 2520 |
| gtnaagccnn tgctncaggt gacacggcag gaggaggaga tgcaggccaa ggaggangag | 2580 |
| ntgcanaaga tcanggagcg ncagcagaag gcngaganng agntnvagga gctgvagcag | 2640 |
| aagcacacnc agctgncnga ggagaagann ctgctgcagg agcagntgca ggcngagacn | 2700 |
| gagctgtang cngagncnga ggagatgcgn gtccggntgg cngccaagaa gcagganctg | 2760 |
| gagganatcc tncatgagat ggaggcccgc ctggaggang aggaagaccg gngccagcan | 2820 |
| ctncaggcng agaggaagaa gatggccagc cagatgctng acctgganga gcaactggag | 2880 |
| gaggangang cngccagnca gaanctacag ctnganaagg tcacngcnga ggccaagatc | 2940 |
| aagaanntgg aggangacat cntggtnatg gangatcaga acannaanct ntcaaaagan | 3000 |
| cgaaaactcc tngaagagag gntnagngan ttnacaacna anctngcnga ngaggaagan | 3060 |
| aaggcnaana acctnacnaa gctgaaganc aagcatgant cnatgatctc aganctggan | 3120 |
| gtgnggctga agaangagga gaagagccgg caggagctgg agaanctnaa gnggaanntg | 3180 |
| ganggngang ccagtgacnt ccangagcag atcgcngacn tncaggcnca gatngcagag | 3240 |
| ctcaagatgc agctggcnaa gaangangan gagctncagg cngcnctngc caggctngan | 3300 |
| gangananngn cncagaanaa caangccctn aagaagatnc gngagctnga gggncanatc | 3360 |
| tcngacctnc angaggacct ngactcagag cgggcngcca gaacaaggc ngaaagcag | 3420 |
| aagcgagacc tnggngagga gctggaggcn ctnaagacng agctgganga nacnctggac | 3480 |
| ancacngcna cncagcagga gctcvgngcc aagngggganc aggaggtgac ngtgctgaag | 3540 |
| aaggccctgg angangagac ncggtcccat gaggcncagg tccaggagat gaggcagaan | 3600 |
| cacncacagg nngtggagga nctcacngag cagctnganc agttcaanag ggccaaggcn | 3660 |
| aacctngaca anancaagca gacnctggag aangagaacg cngacctggc nggngagctg | 3720 |
| cgngtcctgg gccaggcnaa gcaggaggtg gancanaaga agaagaagct ggaggngcag | 3780 |
| ntgcagganc tgcagtccaa gtgcagngat ggggagcgng cccgggcnga gctcanngac | 3840 |
| aangtccaca agctncagaa tgaagtngag agngtcacng gnatgctnan ngaggcngag | 3900 |
| ggnaagccaa tnaanctggc caangangtg gcntccctng gntcccagct ncagganacc | 3960 |
| cangagctgc tncaagaaga aacccggcag aagctcaang tgtcnacnaa gctgcgncag | 4020 |
| ntggangang annggaacag cctgcangan cagctggang aggagatgga ggcnaagcan | 4080 |
| aacctggagc gccanntctc nacnctnaac atncagctct cngactcnaa gaagaagctg | 4140 |
| caggactttg cnagnaccnt ngannnyntg ganganggna agaagaggtt ncagaangan | 4200 |
| atngagnncc tcanccagca gtaygangag aangcngcng cntanganaa actgganaan | 4260 |
| accaagaaca ggctncagca ggagctggan gacctggtng tnganttgga naaccagcgg | 4320 |
| caactngtnt ccaanctgga aaagaagcag angaanttng ancagttgtt agcngaggan | 4380 |
| aanaacatct cntccaanta ncggatgan agngacvgag cngangcnga ngcnagggan | 4440 |
| aagganacna aggcnntgtc nctngcncgg gccctngang angccntgga ngccaaagan | 4500 |
| ganctngagv gnaccaacaa natgctcaan gcnganatgg aagacctngt cagctccaag | 4560 |
| gangangtng caagaacgt ncatganctg gagaagtcca agcgngccnt ggagacncag | 4620 |
| atggangaga tgaanacnca gctggangag yyrgaggang anntgcangc cacngaggan | 4680 |
| gccaanctgc ggntngangt caacatgcag gcnctcaang nccagttnga nvgngatctc | 4740 |

```
cangcncggg angancagaa ngaggagaag aggaggcanc tncagvgnca gctncangag    4800
tangagacng aactggaaga ngancgnaag canvgngcnc tggcngcngc agcnaagaag    4860
aagctggang gggacctnaa agacctngag ctncaggcng actcngccat caangggngg    4920
gaggaagcca tcaagcagct ncnnaaactg caggctcaga tgaaggactt ncanagagan    4980
ctggangatg cccgtgcctc cagngangag atctttgcca cnncaanga gaagagaag     5040 aaagccaaga gnntggangc agacctcatg cagctncaag gganctgc ngcngcngag     5100 agngctcgca ancangcnga cntngagaag gagganctgg cngaggagct ggcnagnagc    5160
ntgtcnggaa ggaanncnct ncaggangag aagcgccgcc tggaggcnng gatcgcncan    5220
ctngaggagg agctggagga ngancagggc aacatggagg cnatgagnga nvgngtncgc    5280
aangcnacnc ngcaggcnga gcanctnagc aangagctgg ccacagancg cagcacngcn    5340
cagaagaatg agagnncncg gcancagctn gagcgncaga acaaggancttnmrnagcaag     5400 ntncangagn tngangngc ngtcaanncc aagntcaant ccacnntngc ggcgctggag     5460
gccaagattg cncagctnga ggagcaggtn gancaggagg ccagagagaa ncaggcggcc    5520
nccaagncgc tgaagcanan ngacaagaag ctnaaggann tnntgctgca ggtggangan    5580
gagcgcaaga tggcngagca gtacaaggag caggcagaga aaggnaannc canggtcaag    5640
cagctnaaga ggcagctgga ngaggcngag gaggagtcnc agngcatcaa cgccaaccgc    5700
aggaagctgc agcgggagct ngangaggcc acngagagca angaggccat gggccgngag    5760
gtgaacgcnc tcaagagcaa nctcaggvga ggaaacgagn cntcnttngt tcctncnaga    5820
aggnctggng gncgtagagt tattgaaaan ncagatggnt ctganganga anbggacnct    5880
cgngacncag acttcaatgg aaccaanncc agtgaatra                          5919
```

<210> SEQ ID NO 3
<211> LENGTH: 1972
<212> TYPE: PRT
<213> ORGANISM: Mus musculus

<400> SEQUENCE: 3

```
Met Ala Gln Lys Gly Gln Leu Ser Asp Asp Glu Lys Phe Leu Phe Val
 1               5                  10                  15

Asp Lys Asn Phe Met Asn Ser Pro Met Ala Gln Ala Asp Trp Val Ala
            20                  25                  30

Lys Lys Leu Val Trp Val Pro Ser Glu Lys Gln Gly Phe Glu Ala Ala
        35                  40                  45

Ser Ile Lys Glu Glu Lys Gly Asp Glu Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Asn Pro Tyr
        115                 120                 125

Lys Tyr Leu Pro Ile Tyr Ser Glu Lys Ile Val Asp Met Tyr Lys Gly
    130                 135                 140

Lys Lys Arg His Glu Met Pro Pro His Ile Tyr Ala Ile Ala Asp Thr
145                 150                 155                 160
```

```
Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Gln Lys Val Ile
            180                 185                 190

Gln Tyr Leu Ala Val Val Ala Ser His Lys Gly Lys Lys Asp Ser
        195                 200                 205

Ser Ile Thr Gly Glu Leu Glu Lys Gln Leu Leu Gln Ala Asn Pro Ile
    210                 215                 220

Leu Glu Ala Phe Gly Asn Ala Lys Thr Val Lys Asn Asp Asn Ser Ser
225                 230                 235                 240

Arg Phe Gly Lys Phe Ile Arg Ile Asn Phe Asp Val Thr Gly Tyr Ile
                245                 250                 255

Val Gly Ala Asn Ile Glu Thr Tyr Leu Leu Glu Lys Ser Arg Ala Ile
            260                 265                 270

Arg Gln Ala Arg Asp Glu Arg Thr Phe His Ile Phe Tyr Tyr Leu Leu
        275                 280                 285

Ala Gly Ala Lys Glu Lys Met Lys Ser Asp Leu Leu Leu Glu Ser Phe
    290                 295                 300

Asn Ser Tyr Thr Phe Leu Ser Asn Gly Phe Val Pro Ile Pro Ala Ala
305                 310                 315                 320

Gln Asp Asp Glu Met Phe Gln Glu Thr Leu Glu Ala Met Ser Ile Met
                325                 330                 335

Gly Phe Asn Glu Glu Glu Gln Leu Ala Ile Leu Lys Val Val Ser Ser
            340                 345                 350

Val Leu Gln Leu Gly Asn Ile Val Phe Lys Lys Glu Arg Asn Thr Asp
        355                 360                 365

Gln Ala Ser Met Pro Asp Asn Thr Ala Ala Gln Lys Val Cys His Leu
    370                 375                 380

Val Gly Ile Asn Val Thr Asp Phe Thr Arg Ala Ile Leu Thr Pro Arg
385                 390                 395                 400

Ile Lys Val Gly Arg Asp Val Val Gln Lys Ala Gln Thr Lys Glu Gln
                405                 410                 415

Ala Asp Phe Ala Ile Glu Ala Leu Ala Lys Ala Thr Tyr Glu Arg Leu
            420                 425                 430

Phe Arg Trp Ile Leu Ser Arg Val Asn Lys Ala Leu Asp Lys Thr His
        435                 440                 445

Arg Gln Gly Ala Ser Phe Leu Gly Ile Leu Asp Ile Ala Gly Phe Glu
    450                 455                 460

Ile Phe Glu Val Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
            500                 505                 510

Leu Asp Leu Gln Pro Ser Ile Glu Leu Ile Glu Arg Pro Asn Asn Pro
        515                 520                 525

Pro Gly Val Leu Ala Leu Leu Asp Glu Glu Cys Trp Phe Pro Lys Ala
    530                 535                 540

Thr Asp Lys Ser Phe Val Glu Lys Leu Cys Ser Glu Gln Gly Asn His
545                 550                 555                 560

Pro Lys Phe Gln Lys Pro Lys Gln Leu Lys Asp Lys Thr Glu Phe Ser
                565                 570                 575

Ile Ile His Tyr Ala Gly Lys Val Asp Tyr Asn Ala Ser Ala Trp Leu
```

-continued

```
                    580                     585                     590
Thr Lys Asn Met Asp Pro Leu Asn Asp Asn Val Thr Ser Leu Leu Asn
                595                     600                     605

Ala Ser Ser Asp Lys Phe Val Ala Asp Leu Trp Lys Asp Val Asp Arg
            610                     615                     620

Ile Val Gly Leu Asp Gln Met Ala Lys Met Thr Glu Ser Ser Leu Pro
625                     630                     635                     640

Ser Ala Ser Lys Thr Lys Lys Gly Met Phe Arg Thr Val Gly Gln Leu
                645                     650                     655

Tyr Lys Glu Gln Leu Gly Lys Leu Met Ala Thr Leu Arg Asn Thr Thr
                660                     665                     670

Ala Asn Phe Val Arg Cys Ile Ile Pro Asn His Glu Lys Arg Ser Gly
                675                     680                     685

Lys Leu Asp Ala Phe Leu Val Leu Glu Gln Leu Arg Cys Asn Gly Val
            690                     695                     700

Leu Glu Gly Ile Arg Ile Cys Arg Gln Gly Phe Pro Asn Arg Ile Val
705                     710                     715                     720

Phe Gln Glu Phe Arg Gln Arg Tyr Glu Ile Leu Ala Ala Asn Ala Ile
                725                     730                     735

Pro Lys Gly Phe Met Asp Gly Lys Gln Ala Cys Ile Leu Met Ile Lys
                740                     745                     750

Ala Leu Glu Leu Asp Pro Asn Leu Tyr Arg Ile Gly Gln Ser Lys Ile
                755                     760                     765

Phe Phe Arg Thr Gly Val Leu Ala His Leu Glu Glu Glu Arg Asp Leu
            770                     775                     780

Lys Ile Thr Asp Val Ile Met Ala Phe Gln Ala Met Cys Arg Gly Tyr
785                     790                     795                     800

Leu Ala Arg Lys Ala Phe Thr Lys Arg Gln Gln Gln Leu Thr Ala Met
                805                     810                     815

Lys Val Ile Gln Arg Asn Cys Ala Ala Tyr Leu Lys Leu Arg Asn Trp
                820                     825                     830

Gln Trp Trp Arg Leu Phe Thr Lys Val Lys Pro Leu Leu Gln Val Thr
            835                     840                     845

Arg Gln Glu Glu Glu Met Gln Ala Lys Glu Glu Met Gln Lys Ile
            850                     855                     860

Thr Glu Arg Gln Gln Lys Ala Glu Thr Glu Leu Lys Glu Leu Glu Gln
865                     870                     875                     880

Lys His Thr Gln Leu Ala Glu Glu Lys Thr Leu Leu Gln Glu Gln Leu
                885                     890                     895

Gln Ala Glu Thr Glu Leu Tyr Ala Glu Ser Glu Met Arg Val Arg
            900                     905                     910

Leu Ala Ala Lys Lys Gln Glu Leu Glu Glu Ile Leu His Glu Met Glu
            915                     920                     925

Ala Arg Leu Glu Glu Glu Glu Asp Arg Arg Gln Gln Leu Gln Ala Glu
            930                     935                     940

Arg Lys Lys Met Ala Gln Met Leu Asp Leu Glu Glu Gln Leu Glu
945                     950                     955                     960

Glu Glu Glu Ala Ala Arg Gln Lys Leu Gln Leu Glu Lys Val Thr Ala
                965                     970                     975

Glu Ala Lys Ile Lys Lys Leu Glu Asp Asp Ile Leu Val Met Asp Asp
            980                     985                     990

Gln Asn Ser Lys Leu Ser Lys Glu Arg Lys Leu Leu Glu Glu Arg Val
            995                     1000                    1005
```

-continued

```
Ser Asp Leu Thr Thr Asn Leu Ala Glu Glu Glu Lys Ala Lys Asn
    1010                1015                1020
Leu Thr Lys Leu Lys Ser Lys His Glu Ser Met Ile Ser Glu Leu Glu
1025                1030                1035                1040
Val Arg Leu Lys Lys Glu Glu Lys Ser Arg Gln Glu Leu Glu Lys Leu
                1045                1050                1055
Lys Arg Lys Leu Glu Gly Asp Ala Ser Asp Phe His Glu Gln Ile Ala
                1060                1065                1070
Asp Leu Gln Ala Gln Ile Ala Glu Leu Lys Met Gln Leu Ala Lys Lys
                1075                1080                1085
Glu Glu Glu Leu Gln Ala Ala Leu Ala Arg Leu Asp Glu Glu Ile Ala
            1090                1095                1100
Gln Lys Asn Asn Ala Leu Lys Lys Ile Arg Glu Leu Glu Gly His Ile
1105                1110                1115                1120
Ser Asp Leu Gln Glu Asp Leu Asp Ser Glu Arg Ala Ala Arg Asn Lys
                1125                1130                1135
Ala Glu Lys Gln Lys Arg Asp Leu Gly Glu Glu Leu Glu Ala Leu Lys
                1140                1145                1150
Thr Glu Leu Glu Asp Thr Leu Asp Ser Thr Ala Thr Gln Gln Glu Leu
                1155                1160                1165
Arg Ala Lys Arg Glu Gln Glu Val Thr Val Leu Lys Lys Ala Leu Asp
            1170                1175                1180
Glu Glu Thr Arg Ser His Glu Ala Gln Val Gln Glu Met Arg Gln Lys
1185                1190                1195                1200
His Thr Gln Ala Val Glu Glu Leu Thr Glu Gln Leu Glu Gln Phe Lys
                1205                1210                1215
Arg Ala Lys Ala Asn Leu Asp Lys Ser Lys Gln Thr Leu Glu Lys Glu
                1220                1225                1230
Asn Ala Asp Leu Ala Gly Glu Leu Arg Val Leu Gly Gln Ala Lys Gln
                1235                1240                1245
Glu Val Glu His Lys Lys Lys Lys Leu Glu Val Gln Leu Gln Asp Leu
            1250                1255                1260
Gln Ser Lys Cys Ser Asp Gly Glu Arg Ala Arg Ala Glu Leu Ser Asp
1265                1270                1275                1280
Lys Val His Lys Leu Gln Asn Glu Val Glu Ser Val Thr Gly Met Leu
                1285                1290                1295
Asn Glu Ala Glu Gly Lys Ala Ile Lys Leu Ala Lys Asp Val Ala Ser
                1300                1305                1310
Leu Gly Ser Gln Leu Gln Asp Thr Gln Glu Leu Leu Gln Glu Glu Thr
            1315                1320                1325
Arg Gln Lys Leu Asn Val Ser Thr Lys Leu Arg Gln Leu Glu Asp Glu
            1330                1335                1340
Arg Asn Ser Leu Gln Asp Gln Leu Asp Glu Glu Met Glu Ala Lys Gln
1345                1350                1355                1360
Asn Leu Glu Arg His Val Ser Thr Leu Asn Ile Gln Leu Ser Asp Ser
                1365                1370                1375
Lys Lys Lys Leu Gln Asp Phe Ala Ser Thr Ile Glu Val Met Glu Glu
            1380                1385                1390
Gly Lys Lys Arg Leu Gln Lys Glu Met Glu Gly Leu Ser Gln Gln Tyr
            1395                1400                1405
Glu Glu Lys Ala Ala Ala Tyr Asp Lys Leu Glu Lys Thr Lys Asn Arg
            1410                1415                1420
```

```
Leu Gln Gln Glu Leu Asp Asp Leu Val Val Asp Leu Asp Asn Gln Arg
1425                1430                1435                1440

Gln Leu Val Ser Asn Leu Glu Lys Lys Gln Lys Lys Phe Asp Gln Leu
            1445                1450                1455

Leu Ala Glu Glu Lys Asn Ile Ser Ser Lys Tyr Ala Asp Glu Arg Asp
                1460                1465                1470

Arg Ala Glu Ala Glu Ala Arg Glu Lys Glu Thr Lys Ala Leu Ser Leu
    1475                1480                1485

Ala Arg Ala Leu Glu Glu Ala Leu Glu Ala Lys Glu Glu Leu Glu Arg
    1490                1495                1500

Thr Asn Lys Met Leu Lys Ala Glu Met Glu Asp Leu Val Ser Ser Lys
1505                1510                1515                1520

Asp Asp Val Gly Lys Asn Val His Glu Leu Glu Lys Ser Lys Arg Ala
            1525                1530                1535

Leu Glu Thr Gln Met Glu Glu Met Lys Thr Gln Leu Glu Glu Ser Glu
                1540                1545                1550

Asp Asp Val Gln Ala Thr Glu Asp Ala Lys Leu Arg Leu Glu Val Asn
    1555                1560                1565

Met Gln Ala Leu Lys Gly Gln Phe Glu Arg Asp Leu Gln Ala Arg Asp
    1570                1575                1580

Glu Gln Asn Glu Glu Lys Arg Arg Gln Leu Gln Arg Gln Leu His Glu
1585                1590                1595                1600

Tyr Glu Thr Glu Leu Glu Asp Glu Arg Lys Gln Arg Ala Leu Ala Ala
            1605                1610                1615

Ala Ala Lys Lys Lys Leu Glu Gly Asp Leu Lys Asp Leu Glu Leu Gln
                1620                1625                1630

Ala Asp Ser Ala Ile Lys Gly Arg Glu Glu Ala Ile Lys Gln Leu Arg
    1635                1640                1645

Lys Leu Gln Ala Gln Met Lys Asp Phe Gln Arg Glu Leu Asp Asp Ala
    1650                1655                1660

Arg Ala Ser Arg Asp Glu Ile Phe Ala Thr Ser Lys Glu Asn Glu Lys
1665                1670                1675                1680

Lys Ala Lys Ser Leu Glu Ala Asp Leu Met Gln Leu Gln Glu Asp Leu
            1685                1690                1695

Ala Ala Ala Glu Arg Ala Arg Lys Gln Ala Asp Leu Glu Lys Glu Glu
                1700                1705                1710

Leu Ala Glu Glu Leu Ala Ser Ser Leu Ser Gly Arg Asn Thr Leu Gln
    1715                1720                1725

Asp Glu Lys Arg Arg Leu Glu Ala Arg Ile Ala Gln Leu Glu Glu Glu
    1730                1735                1740

Leu Glu Glu Glu Gln Gly Asn Met Glu Ala Met Ser Asp Arg Val Arg
1745                1750                1755                1760

Lys Ala Thr Leu Gln Ala Glu Gln Leu Ser Asn Glu Leu Ala Thr Glu
            1765                1770                1775

Arg Ser Thr Ala Gln Lys Asn Glu Ser Ala Arg Gln Gln Leu Glu Arg
                1780                1785                1790

Gln Asn Lys Glu Leu Arg Ser Lys Leu Gln Glu Val Glu Gly Ala Val
    1795                1800                1805

Lys Ala Lys Leu Lys Ser Thr Val Ala Ala Leu Glu Ala Lys Ile Ala
    1810                1815                1820

Gln Leu Glu Glu Gln Val Glu Gln Glu Ala Arg Glu Lys Gln Ala Ala
1825                1830                1835                1840

Thr Lys Ser Leu Lys Gln Lys Asp Lys Lys Leu Lys Glu Val Leu Leu
```

```
                    1845                1850                1855

Gln Val Glu Asp Glu Arg Lys Met Ala Glu Gln Tyr Lys Glu Gln Ala
            1860                1865                1870

Glu Lys Gly Asn Thr Lys Val Lys Gln Leu Lys Arg Gln Leu Glu Glu
        1875                1880                1885

Ala Glu Glu Glu Ser Gln Cys Ile Asn Ala Asn Arg Arg Lys Leu Gln
    1890                1895                1900

Arg Glu Leu Asp Glu Ala Thr Glu Ser Asn Glu Ala Met Gly Arg Glu
1905                1910                1915                1920

Val Asn Ala Leu Lys Ser Lys Leu Arg Arg Gly Asn Glu Ala Ser Phe
                1925                1930                1935

Val Pro Ser Arg Arg Ala Gly Gly Arg Arg Val Ile Glu Asn Thr Asp
            1940                1945                1950

Gly Ser Glu Glu Glu Met Asp Ala Arg Asp Ser Asp Phe Asn Gly Thr
        1955                1960                1965

Lys Ala Ser Glu
    1970

<210> SEQ ID NO 4
<211> LENGTH: 1972
<212> TYPE: PRT
<213> ORGANISM: Oryctolagus cuniculus

<400> SEQUENCE: 4

Met Ala Gln Lys Gly Gln Leu Ser Asp Asp Glu Lys Phe Leu Phe Val
 1               5                  10                  15

Asp Lys Asn Phe Ile Asn Ser Pro Val Ala Gln Ala Asp Trp Val Ala
            20                  25                  30

Lys Arg Leu Val Trp Val Pro Ser Glu Lys Gln Gly Phe Glu Ala Ala
        35                  40                  45

Ser Ile Lys Glu Glu Lys Gly Asp Glu Val Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Asn Pro Tyr
        115                 120                 125

Lys Gln Leu Pro Ile Tyr Ser Glu Lys Ile Val Asp Met Tyr Lys Gly
    130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala Val Val Ala Ser Ser His Lys Gly Lys Lys Asp Thr
        195                 200                 205

Ser Ile Thr Gly Glu Leu Glu Lys Gln Leu Leu Gln Ala Asn Pro Ile
    210                 215                 220

Leu Glu Ala Phe Gly Asn Ala Lys Thr Val Lys Asn Asp Asn Ser Ser
225                 230                 235                 240
```

-continued

```
Arg Phe Gly Lys Phe Ile Arg Ile Asn Phe Asp Val Thr Gly Tyr Ile
            245                 250                 255

Val Gly Ala Asn Ile Glu Thr Tyr Leu Leu Glu Lys Ser Arg Ala Ile
        260                 265                 270

Arg Gln Ala Arg Glu Glu Arg Thr Phe His Ile Phe Tyr Tyr Leu Ile
    275                 280                 285

Ala Gly Ala Lys Glu Lys Met Arg Asn Asp Leu Leu Leu Glu Gly Phe
290                 295                 300

Asn Asn Tyr Thr Phe Leu Ser Asn Gly Phe Val Pro Ile Pro Ala Ala
305                 310                 315                 320

Gln Asp Asp Glu Met Phe Gln Glu Thr Val Glu Ala Met Ser Ile Met
                325                 330                 335

Gly Phe Ser Glu Glu Gln Leu Ser Val Leu Lys Val Val Ser Ser
                340                 345                 350

Val Leu Gln Leu Gly Asn Ile Val Phe Lys Lys Glu Arg Asn Thr Asp
            355                 360                 365

Gln Ala Ser Met Pro Asp Asn Thr Ala Ala Gln Lys Val Cys His Leu
    370                 375                 380

Met Gly Ile Asn Val Thr Asp Phe Thr Arg Ser Ile Leu Thr Pro Arg
385                 390                 395                 400

Ile Lys Val Gly Arg Asp Val Val Gln Lys Ala Gln Thr Lys Glu Gln
                405                 410                 415

Ala Asp Phe Ala Val Glu Ala Leu Ala Lys Ala Thr Tyr Glu Arg Leu
            420                 425                 430

Phe Arg Trp Ile Leu Ser Arg Val Asn Lys Ala Leu Asp Lys Thr His
        435                 440                 445

Arg Gln Gly Ala Ser Phe Leu Gly Ile Leu Asp Ile Ala Gly Phe Glu
    450                 455                 460

Ile Phe Glu Val Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
            500                 505                 510

Leu Asp Leu Gln Pro Cys Ile Glu Leu Ile Glu Arg Pro Asn Asn Pro
        515                 520                 525

Pro Gly Val Leu Ala Leu Leu Asp Glu Glu Cys Trp Phe Pro Lys Ala
    530                 535                 540

Thr Asp Lys Ser Phe Val Glu Lys Leu Cys Thr Glu Gln Gly Asn His
545                 550                 555                 560

Pro Lys Phe Gln Lys Pro Lys Gln Leu Lys Asp Lys Thr Glu Phe Ser
                565                 570                 575

Ile Ile His Tyr Ala Gly Lys Val Asp Tyr Asn Ala Ser Ala Trp Leu
            580                 585                 590

Thr Lys Asn Met Asp Pro Leu Asn Asp Asn Val Thr Ser Leu Leu Asn
        595                 600                 605

Ala Ser Ser Asp Lys Phe Val Ala Asp Leu Trp Lys Asp Val Asp Arg
    610                 615                 620

Ile Val Gly Leu Asp Gln Met Ala Lys Met Thr Glu Ser Ser Leu Pro
625                 630                 635                 640

Ser Ala Ser Lys Thr Lys Lys Gly Met Phe Arg Thr Val Gly Gln Leu
                645                 650                 655

Tyr Lys Glu Gln Leu Gly Lys Leu Met Thr Thr Leu Arg Asn Thr Thr
```

-continued

```
                660                 665                 670
Pro Asn Phe Val Arg Cys Ile Ile Pro Asn His Glu Lys Arg Ser Gly
                675                 680                 685
Lys Leu Asp Ala Phe Leu Val Leu Glu Gln Leu Arg Cys Asn Gly Val
690                 695                 700
Leu Glu Gly Ile Arg Ile Cys Arg Gln Gly Phe Pro Asn Arg Ile Val
705                 710                 715                 720
Phe Gln Glu Phe Arg Gln Arg Tyr Glu Ile Leu Ala Ala Asn Ala Ile
                725                 730                 735
Pro Lys Gly Phe Met Asp Gly Lys Gln Ala Cys Ile Leu Met Ile Lys
                740                 745                 750
Ala Leu Glu Leu Asp Pro Asn Leu Tyr Arg Ile Gly Gln Ser Lys Ile
                755                 760                 765
Phe Phe Arg Thr Gly Val Leu Ala His Leu Glu Glu Arg Asp Leu
770                 775                 780
Lys Ile Thr Asp Val Ile Met Ala Phe Gln Ala Met Cys Arg Gly Tyr
785                 790                 795                 800
Leu Ala Arg Lys Ala Phe Ala Lys Arg Gln Gln Gln Leu Thr Ala Met
                805                 810                 815
Lys Val Ile Gln Arg Asn Cys Ala Ala Tyr Leu Lys Leu Arg Asn Trp
                820                 825                 830
Gln Trp Trp Arg Leu Phe Thr Lys Val Lys Pro Leu Leu Gln Val Thr
                835                 840                 845
Arg Gln Glu Glu Glu Met Gln Ala Lys Glu Asp Glu Leu Gln Lys Ile
                850                 855                 860
Lys Glu Arg Gln Gln Lys Ala Glu Ser Glu Leu Gln Glu Leu Gln Gln
865                 870                 875                 880
Lys His Thr Gln Leu Ser Glu Glu Lys Asn Leu Leu Gln Glu Gln Leu
                885                 890                 895
Gln Ala Glu Thr Glu Leu Tyr Ala Glu Ala Glu Glu Met Arg Val Arg
                900                 905                 910
Leu Ala Ala Lys Lys Gln Glu Leu Glu Glu Ile Leu His Glu Met Glu
                915                 920                 925
Ala Arg Leu Glu Glu Glu Glu Asp Arg Gly Gln Gln Leu Gln Ala Glu
                930                 935                 940
Arg Lys Lys Met Ala Gln Gln Met Leu Asp Leu Glu Glu Gln Leu Glu
945                 950                 955                 960
Glu Glu Glu Ala Ala Arg Gln Lys Leu Gln Leu Glu Lys Val Thr Ala
                965                 970                 975
Glu Ala Lys Ile Lys Lys Leu Glu Asp Asp Ile Leu Val Met Asp Asp
                980                 985                 990
Gln Asn Asn Lys Leu Ser Lys Glu Arg Lys Leu Leu Glu Glu Arg Ile
                995                 1000                1005
Ser Asp Leu Thr Thr Asn Leu Ala Glu Glu Glu Lys Ala Lys Asn
    1010                1015                1020
Leu Thr Lys Leu Lys Asn Lys His Glu Ser Met Ile Ser Glu Leu Glu
1025                1030                1035                1040
Val Arg Leu Lys Lys Glu Glu Lys Ser Arg Gln Glu Leu Glu Lys Leu
                1045                1050                1055
Lys Arg Lys Met Asp Gly Glu Ala Ser Asp Leu His Glu Gln Ile Ala
                1060                1065                1070
Asp Leu Gln Ala Gln Ile Ala Glu Leu Lys Met Gln Leu Ala Lys Lys
                1075                1080                1085
```

-continued

```
Glu Glu Glu Leu Gln Ala Ala Leu Ala Arg Leu Glu Asp Glu Thr Ser
    1090                1095                1100
Gln Lys Asn Asn Ala Leu Lys Lys Ile Arg Glu Leu Glu Gly His Ile
1105                1110                1115                1120
Ser Asp Leu Gln Glu Asp Leu Asp Ser Glu Arg Ala Ala Arg Asn Lys
                1125                1130                1135
Ala Glu Lys Gln Lys Arg Asp Leu Gly Glu Glu Leu Glu Ala Leu Lys
            1140                1145                1150
Thr Glu Leu Glu Asp Thr Leu Asp Thr Thr Ala Thr Gln Gln Glu Leu
        1155                1160                1165
Arg Ala Lys Arg Glu Gln Glu Val Thr Val Leu Lys Lys Ala Leu Asp
    1170                1175                1180
Glu Glu Thr Arg Ser His Glu Ala Gln Val Gln Glu Met Arg Gln Lys
1185                1190                1195                1200
His Thr Gln Val Val Glu Glu Leu Thr Glu Gln Leu Glu Gln Phe Lys
                1205                1210                1215
Arg Ala Lys Ala Asn Leu Asp Lys Thr Lys Gln Thr Leu Glu Lys Glu
            1220                1225                1230
Asn Ala Asp Leu Ala Gly Glu Leu Arg Val Leu Gly Gln Ala Lys Gln
        1235                1240                1245
Glu Val Glu His Lys Lys Lys Lys Leu Glu Val Gln Leu Gln Glu Leu
    1250                1255                1260
Gln Ser Lys Cys Ser Asp Gly Glu Arg Ala Arg Ala Glu Leu Asn Asp
1265                1270                1275                1280
Lys Val His Lys Leu Gln Asn Glu Val Glu Ser Val Thr Gly Met Leu
                1285                1290                1295
Ser Glu Ala Glu Gly Lys Ala Ile Lys Leu Ala Lys Glu Val Ala Ser
            1300                1305                1310
Leu Gly Ser Gln Leu Gln Asp Thr Gln Glu Leu Leu Gln Glu Glu Thr
        1315                1320                1325
Arg Gln Lys Leu Asn Val Ser Thr Lys Leu Arg Gln Leu Glu Asp Glu
    1330                1335                1340
Arg Asn Ser Leu Gln Glu Gln Leu Asp Glu Glu Met Glu Ala Lys Gln
1345                1350                1355                1360
Asn Leu Glu Arg His Ile Ser Thr Leu Asn Ile Gln Leu Ser Asp Ser
                1365                1370                1375
Lys Lys Lys Leu Gln Asp Phe Ala Ser Thr Val Glu Ser Leu Glu Glu
            1380                1385                1390
Gly Lys Lys Arg Phe Gln Lys Glu Ile Glu Ser Leu Thr Gln Gln Tyr
        1395                1400                1405
Glu Glu Lys Ala Ala Ala Tyr Asp Lys Leu Glu Lys Thr Lys Asn Arg
    1410                1415                1420
Leu Gln Gln Glu Leu Asp Asp Leu Val Val Asp Leu Asp Asn Gln Arg
1425                1430                1435                1440
Gln Leu Val Ser Asn Leu Glu Lys Lys Gln Lys Lys Phe Asp Gln Leu
                1445                1450                1455
Leu Ala Glu Glu Lys Asn Ile Ser Ser Lys Tyr Ala Asp Glu Arg Asp
            1460                1465                1470
Arg Ala Glu Ala Glu Ala Arg Glu Lys Glu Thr Lys Ala Leu Ser Leu
        1475                1480                1485
Ala Arg Ala Leu Glu Glu Ala Leu Glu Ala Lys Glu Glu Leu Glu Arg
    1490                1495                1500
```

```
Thr Asn Lys Met Leu Lys Ala Glu Met Glu Asp Leu Val Ser Ser Lys
1505                1510                1515                1520

Asp Asp Val Gly Lys Asn Val His Glu Leu Glu Lys Ser Lys Arg Ala
            1525                1530                1535

Leu Glu Thr Gln Met Glu Glu Met Lys Thr Gln Leu Glu Glu Leu Glu
                1540                1545                1550

Asp Glu Leu Gln Ala Thr Glu Asp Ala Lys Leu Arg Leu Glu Val Asn
        1555                1560                1565

Met Gln Ala Leu Lys Val Gln Phe Glu Arg Asp Leu Gln Ala Arg Asp
1570                1575                1580

Glu Gln Asn Glu Glu Lys Arg Arg Gln Leu Gln Arg Gln Leu His Glu
1585                1590                1595                1600

Tyr Glu Thr Glu Leu Glu Asp Glu Arg Lys Gln Arg Ala Leu Ala Ala
                1605                1610                1615

Ala Ala Lys Lys Lys Leu Glu Gly Asp Leu Lys Asp Leu Glu Leu Gln
                1620                1625                1630

Ala Asp Ser Ala Ile Lys Gly Arg Glu Glu Ala Ile Lys Gln Leu Leu
        1635                1640                1645

Lys Leu Gln Ala Gln Met Lys Asp Phe Gln Arg Glu Leu Glu Asp Ala
1650                1655                1660

Arg Ala Ser Arg Asp Glu Ile Phe Ala Thr Ala Lys Glu Asn Glu Lys
1665                1670                1675                1680

Lys Ala Lys Ser Leu Glu Ala Asp Leu Met Gln Leu Gln Glu Asp Leu
                1685                1690                1695

Ala Ala Ala Glu Arg Ala Arg Lys Gln Ala Asp Leu Glu Lys Glu Glu
                1700                1705                1710

Leu Ala Glu Glu Leu Ala Ser Ser Leu Ser Gly Arg Asn Ala Leu Gln
        1715                1720                1725

Asp Glu Lys Arg Arg Leu Glu Ala Arg Ile Ala Gln Leu Glu Glu Glu
        1730                1735                1740

Leu Glu Glu Glu Gln Gly Asn Met Glu Ala Met Ser Asp Arg Val Arg
1745                1750                1755                1760

Lys Ala Thr Gln Gln Ala Glu Gln Leu Ser Asn Glu Leu Ala Thr Glu
        1765                1770                1775

Arg Ser Thr Ala Gln Lys Asn Glu Ser Ala Arg Gln Gln Leu Glu Arg
        1780                1785                1790

Gln Asn Lys Glu Leu Lys Ser Lys Leu Gln Glu Met Glu Gly Ala Val
        1795                1800                1805

Lys Ser Lys Phe Lys Ser Thr Ile Ala Ala Leu Glu Ala Lys Ile Ala
1810                1815                1820

Gln Leu Glu Glu Gln Val Glu Gln Glu Ala Arg Glu Lys Gln Ala Ala
1825                1830                1835                1840

Ala Lys Ala Leu Lys Gln Arg Asp Lys Lys Leu Lys Glu Met Leu Leu
            1845                1850                1855

Gln Val Glu Asp Glu Arg Lys Met Ala Glu Gln Tyr Lys Glu Gln Ala
                1860                1865                1870

Glu Lys Gly Asn Ala Lys Val Lys Gln Leu Lys Arg Gln Leu Glu Glu
        1875                1880                1885

Ala Glu Glu Glu Ser Gln Arg Ile Asn Ala Asn Arg Arg Lys Leu Gln
        1890                1895                1900

Arg Glu Leu Asp Glu Ala Thr Glu Ser Asn Glu Ala Met Gly Arg Glu
1905                1910                1915                1920

Val Asn Ala Leu Lys Ser Lys Leu Arg Arg Gly Asn Glu Thr Ser Phe
```

```
                   1925              1930              1935
Val Pro Thr Arg Arg Ser Gly Gly Arg Arg Val Ile Glu Asn Ala Asp
            1940              1945              1950
Gly Ser Glu Glu Glu Val Asp Ala Arg Asp Ala Asp Phe Asn Gly Thr
            1955              1960              1965
Lys Ser Ser Glu
    1970

<210> SEQ ID NO 5
<211> LENGTH: 6644
<212> TYPE: DNA
<213> ORGANISM: Oryctolagus cuniculus

<400> SEQUENCE: 5
agccttggac gccccggcct gggaggtgtg ccagacccgc gctccccgtc cagtttctcc     60
gcgcgccccc cacttggagg ggaccaacca ggcaccatgg cgcagaaggg ccaactcagc    120
gacgatgaga agttcctctt tgtggacaag aacttcatca cagcccccgt ggcccaggcc    180
gactgggtgg ccaagaggct ggtgtgggtc cttcggaga  agcagggctt cgaggcggcc    240
agcatcaagg aggagaaggg ggatgaggtg gtcgtggagc tggtggagaa tgggaagaag    300
gtcacggtgg gcaaggatga catccagaag atgaacccgc ccaagttctc caaggtggaa    360
gacatggcgg agctgacgtg tctcaacgaa gcttccgtgc tgcacaacct gagggagagg    420
tacttctctg ggctcatcta cacgtactcc ggcctcttct gcgtggtggt caaccccctac   480
aagcagctgc ccatctactc ggagaagatc gtggacatgt acaagggcaa gaagaggcac    540
gagatgccac cacacatcta cgccatcgcc gacacggcct acaggagcat gctgcaggat    600
cgggaggacc agtccattct ctgcacaggc gagtctggag ccgggaagac ggagaacacc    660
aagaaagtca tccagtacct ggccgtggtg gcctcctcgc acaagggcaa gaaggacacg    720
agcatcacgg gggagctgga gaagcagctt ctgcaagcaa accccatcct ggaggccttt    780
ggcaacgcca agacggtcaa gaatgacaac tcctcgcgat tcggcaagtt catccgcatc    840
aactttgacg tcactggtta catcgtgggc gccaacattg agacctatct gctggaaaag    900
tcacgagcca tccgccaagc cgagaggag  ggaccttcc  acatcttttta ctacctgatt    960
gctggggcca aggagaagat gagaaatgac ttgctcttgg agggcttcaa caactacaca   1020
ttcctctcca atggctttgt gcccatccca gccgcccagg atgacgagat gttccaggaa   1080
acggtggagg ccatgtccat catgggcttc agtgaagagg agcagctgtc tgtgttgaag   1140
gtggtgtctt cagtcctgca gcttggaaac atcgtcttca agaaggaaag aaacacagac   1200
caggcgtcca tgccggacaa cacagctgcc cagaaagttt gccacctcat gggaattaac   1260
gtgacagatt tcaccagatc catcctgacc ccgcgtatca agttggacg  ggacgtagtg   1320
cagaaagctc agacaaaaga acaggcagac ttcgctgtcg aggctttggc aaaggccacg   1380
tatgaacgcc ttttccgctg atcctcagc cgtgtgaaca agccctgga  caagacccat   1440
cggcaggggg cttccttcct ggggatcctg gacatcgctg gatttgagat ctttgaggtg   1500
aactccttcg agcagctgtg catcaactac accaacgaga gctgcagca gctgttcaac   1560
cacaccatgt tcatcctgga gcaggaggag taccagcgcg agggcatcga gtggaacttc   1620
atcgacttcg ggctcgacct gcagccctgc attgagctca ttgagcggcc gaacaaccct   1680
ccaggtgtgc tggccctgct ggatgaggag tgctggttcc ccaaagccac agataagtct   1740
tttgtggaga agctgtgcac agagcaaggc aaccacccca agttccagaa gcccaagcag   1800
```

-continued

```
ctcaaggaca aaacggagtt ctccatcatc cattacgctg ggaaggtgga ctacaacgcg      1860
agtgcctggc tgaccaagaa catggacccc ctgaatgaca acgtgacctc cctcctcaac      1920
gcctcctcgg acaagttcgt ggccgaccta tggaaggacg tggaccgcat cgtggggctg      1980
gaccagatgg ccaagatgac agagagctca ctgcccagcg cctccaagac caagaagggc      2040
atgttccgca cggtggggca gctgtacaag gagcagctgg ggaagctgat gaccacgctg      2100
cgcaacacca cgcccaactt cgtgcgctgc atcatcccca accacgagaa gcggtccggc      2160
aagctggacg cgttcctggt gctggagcag ctgcggtgca acggggtgct ggaaggcatc      2220
cgaatctgcc gccagggctt ccccaacagg atcgtcttcc aggagttccg ccaacgctac      2280
gagatcctgg cagccaacgc catccccaag ggcttcatgg atgggaagca agcctgcatt      2340
ctcatgatca aagctctgga actggacccc aacttgtaca ggatcgggca gagcaaaatc      2400
ttcttccgca cgggcgtgct ggcccacctg gaggaggagc gggacttgaa gatcaccgac      2460
gtcatcatgg ccttccaggc catgtgtcgt ggctacctcg cccgcaaggc cttcgccaag      2520
cggcagcagc agctgaccgc catgaaggtg atccagagga actgcgccgc ctacctgaag      2580
ctgcggaact ggcagtggtg cgcctcttc accaaggtga agccgctgct gcaggtgaca      2640
cggcaggagg aggagatgca ggccaaggag gatgagctgc agaagatcaa ggagcgacag      2700
cagaaggcgg agagcgagct ccaggagctg cagcagaagc acacgcagct gtccgaggag      2760
aagaacctgc tgcaggagca gctgcaggcg gagacggagc tgtacgcgga ggccgaggag      2820
atgcgcgtcc ggctggcggc caagaagcag gagctggagg aaatcctgca tgagatggag      2880
gcccgcctgg aggaggagga agaccggggc cagcagctgc aggccgagag gaagaagatg      2940
gcccagcaga tgctggacct ggaagagcaa ctggaggagg aggaagctgc caggcagaag      3000
ctacagctcg aaaaggtcac cgccgaggcc aagatcaaga agttggagga cgacatcctg      3060
gtcatggacg atcagaacaa caagctctca aaagagcgaa actcctgga agagaggatt      3120
agtgatttaa caacaaatct gccgaggag aagagaagg ccaagaacct gaccaagctg      3180
aagaacaagc atgaatccat gatctcagaa ctggaagtgc ggctgaagaa ggaggagaag      3240
agccggcagg agctggagaa gctgaagcgg aagatggacg gcgaggccag tgacctccac      3300
gagcagatcg ccgacctcca ggcgcagatc gcagagctca gatgcagct ggccaagaag      3360
gaagaggagc tgcaggcggc cctggccagg ctggaggatg aaacgtctca gaagaacaac      3420
gccctgaaga gatccgggga gctggagggg cacatctccg acctgcagga ggacctggac      3480
tcagagcggg ccgccaggaa caaggccgag aagcagaagc gagacctggg ggaggagctg      3540
gaggcgctga gacgagct ggaggacacg ctggacacca cggccaccca gcaggagctc      3600
cgggccaagc gggagcagga ggtgacggtg ctgaagaagg ccctggacga ggagacccgg      3660
tcccatgagg cccaggtcca ggagatgagg cagaaacaca cacaggtggt ggaggagctc      3720
acggagcagc tggaacagtt caagagggcc aaggcgaacc tcgacaagac caagcagacg      3780
ctggagaagg agaacgcaga cctggccggc gagctgcggg tcctgggcca ggccaagcag      3840
gaggtggagc acaagaagaa gaagctggag gtgcagctgc aggagctgca gtccaagtgc      3900
agcgatgggg agcgggcccg ggcggagctc aacgacaagg tccacaagct gcagaatgaa      3960
gtggagagcg tcacgggcat gctcagcgag gccgagggga aggccatcaa gctggccaag      4020
gaggtggcgt ccctcgggtc ccagctccag gataccagg agctgctcca agaagaaacc      4080
cggcagaagc tcaacgtgtc caccaagctg cggcagctga aggacgagag gaacagcctg      4140
caggagcagc tggacgagga gatggaggcc aagcagaacc tggagcgcca catctccacc      4200
```

-continued

```
ctgaacatcc agctctccga ctcaaagaag aagctgcagg actttgccag caccgtggag    4260
tccttggagg aaggcaagaa gaggttccag aaggaaattg agagcctcac ccagcagtac    4320
gaagagaaag cagctgctta cgataaactg gaaaagacca gaacaggct tcagcaggag     4380 ctggacgacc tggtcgtaga cttggataac cagcggcaac tggtgtccaa cctggaaaag   4440
aagcagaaga agttcgatca gttgttagcc gaggaaaaga acatctcttc caagtatgcg   4500
gatgaaaggg accgagccga ggctgaagca agggaaaagg aaaccaaggc cttgtccctg   4560
gctcgggccc tcgaggaggc cttggaggcc aagaggagc tcgagagaac caacaaaatg    4620
ctcaaggccg agatggaaga cctcgtcagc tccaaggacg acgtgggcaa gaacgtccat   4680
gagctggaga agtccaagcg ggccctggag acacagatgg aggagatgaa gacgcagctg   4740
gaagagctag aggacgagct gcaggccacc gaggacgcca agctgcggtt ggaggtcaac   4800
atgcaggccc tcaaagtcca gttcgagcgg gatctccagg cccgggatga gcagaacgag   4860
gagaagagga ggcagctgca gaggcagctg catgagtacg acggaact ggaagacgag     4920 cgcaagcagc gggccctggc cgcggcagcc aagaagaagc tggaggggga cctgaaagac   4980
ctggagcttc aggcggactc cgccatcaaa gggcgggagg aagccatcaa gcagcttctg   5040
aaactgcagg ctcagatgaa ggacttccag agagaactgg aagatgcccg tgcctccaga   5100
gacgagatct ttgccacagc caaggagaac gagaagaaag ccaagagtct ggaggcagac   5160
ctcatgcagc tacaagagga tctggccgcg cagagagggc tcgcaaaca ggcagacttg    5220 gagaaggagg agctggccga ggagctggcc agcagcttgt ccggaaggaa cgcgctgcag   5280
gatgagaagc gccgcctgga ggcccggatc gcacagctgg aggaggagct ggaggaggaa   5340
cagggcaaca tggaggcaat gagcgaccgc gtccgcaagg ctacgcagca ggccgagcag   5400
ctcagcaacg agctggccac agagcgcagc acagcccaga gaatgagag cgcacggcag   5460 cagctcgagc ggcagaacaa ggagctcaag agcaagctgc aggagatgga ggggcagtc    5520 aagtccaagt tcaagtccac tatcgcggcg ctggaggcca agattgcgca gctggaggag   5580
caggttgagc aggaggccag agagaagcag gcggccgcca aggcgctgaa gcagagggac   5640
aagaagctga aggagatgct gctgcaggtg gaagacgagc gcaagatggc tgagcagtac   5700
aaggagcagg cagagaaagg aaacgccaag gtcaagcagc tcaagaggca gctggaggag   5760
gccgaggagg agtcgcagcg catcaacgcc aaccgcagga gctgcagcg ggagctggac    5820 gaggccacgg agagcaacga ggccatgggc cgcgaggtga acgcgctcaa gagcaagctc   5880
aggcgaggaa acgagacctc gttcgttcct accagaaggt ctggagggcg tagagttatt   5940
gaaaacgcag atggctctga ggaggaagtg gacgctcgcg acgcagactt caatggaacc   6000
aaatccagtg aatgaacgac ttcgagtttt gcaccacagc agaaggtccc accaaagaac   6060
agattcaacc aaacccaacc cagcaaaccc tacttagcat cgtccaaccc tgtcttcaag   6120
tttcaaacat cacggacaac cccagaacat aaaaaccact gcctgagtca gggtacagaa   6180
ttccaagttt ttatgatgtg gcagaggaaa agccaacga gaacaaaaac accctcgctc    6240
taccgatcag gcagagatgt taagtttttt ggaagataca gccacatgaa ccggtcactg   6300
gtcaattcgt ttacatgaca tgggtgaagt tcaccacgat gggtgccgct gccccactcc   6360
cactcccagt tcattcccta acctctgtgc ccttccaagc ccctgagtaa ggccctggtt   6420
tgagaatccc ttctccctct cctggctacc acacctcaga catgcacagt tcaccccgcc   6480
caagtgcctt ctgtagtcac aagaagtaaa aaaggagaca ctgttccatg gatgagaaca   6540
```

-continued

```
gggacggtcc actgtcttat gtgcacccaa ttgtacttcg gacaccttca ctaataaaag       6600
gtcatacgtc aaaaaaaaaa aaaaaaaaaa ctcgtgccga attc                        6644
```